United States Patent [19]
Burkholder et al.

[11] Patent Number: 5,861,417
[45] Date of Patent: Jan. 19, 1999

[54] HETEROCYCLIC SUBSTITUTED PYRROLIDINE AMIDE DERIVATIVES

[75] Inventors: Timothy P. Burkholder, Carmel, Ind.; George D. Maynard, Westbrook; Elizabeth M. Kudlacz, Groton, both of Conn.

[73] Assignee: Hoechst Marion Roussel, Inc., Cincinnati, Ohio

[21] Appl. No.: 990,672

[22] Filed: Dec. 15, 1997

Related U.S. Application Data

[60] Provisional application No. 60/067,213, Dec. 19, 1996.
[51] Int. Cl.$^6$ ........................ A61K 31/445; C07D 401/14
[52] U.S. Cl. ............................................ 514/326; 546/210
[58] Field of Search .............................. 514/326; 546/210

[56] References Cited

U.S. PATENT DOCUMENTS

| | | | |
|---|---|---|---|
| 5,236,921 | 8/1993 | Emonds-Alt | 514/252 |
| 5,317,020 | 5/1994 | Emonds-Alt | 514/255 |
| 5,340,822 | 8/1994 | Emonds-Alt | 514/316 |
| 5,446,052 | 8/1995 | Emonds-Alt | 514/318 |
| 5,635,510 | 6/1997 | Burkholder et al. | 514/278 |

FOREIGN PATENT DOCUMENTS

| | | |
|---|---|---|
| 1490995 | 3/1995 | Australia . |
| 0512901 | 4/1992 | European Pat. Off. . |
| 0714891 | 11/1995 | European Pat. Off. . |
| 9426735 | 11/1994 | WIPO . |
| 9508549 | 3/1995 | WIPO . |
| 9719074 | 5/1997 | WIPO . |

OTHER PUBLICATIONS

Barnes, et al., TIPS 11:185–189 (May/1990).
Ichinose, et al., The Lancet 340:1248–1251 (Nov. 21, 1992).
Cammack, et al., J. Heterocyclic Chem., 23 73 (1986).
Kudlacz, et al., "In Vitro and in vivo characterization of MDL 105,212A, a nonpepetide NK–1/NK–2 tachykinin rectptor Antagonist", J. Pharm. & Exp. Ther., 277 (2) 840–851 (1996).

Burkholder, et al., "Identification and chemical synthesis of MDL 102,212, a non–peptide tachykinin atnagonist with high affinity for NK1 and NK2 receptaors", Bioorganic & Med. Chem. Letters, 6 (8), 951–956 (1996).

Kudlacz, et al., "The NK–1/NK–2 tachykinin receptor antagonist MDL 105,172A inhibits capsaicin–induced respiratory effects in guinea pigs", 8th Inter. Con., Inflammation Res. Assoc., 1996.

Burkholder, et al., "NK1/NK2 receptor antagonists", Tachykinins & their Antagonists Conference, 1996.

Burkholder, et al., "Identification and chemical synthesis of MDL 105212 a non–selective nonpeptide tachykinis receptor antagonist", Tachykinins '95 from Basic Science Clinical to Application Conference, 1995.

Bioorganic & Med. Chem, Letters, 6(9), 1015–1020 (1996).

J. Med. Chem, 38, 4985–4992 (1995).

*Primary Examiner*—Ceila Chang
*Attorney, Agent, or Firm*—David M. Stemerick

[57] ABSTRACT

The present invention relates to novel heterocyclic substituted pyrrolidine amide derivatives of formula (1),

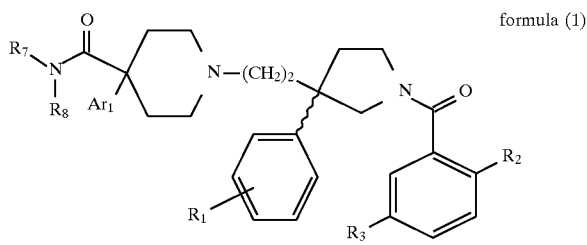

formula (1)

and stereoisomers and pharmaceutically acceptable salts thereof and their use as tachykinin receptor antagonists. Such antagonists are useful in the treatment of tachykinin-mediated diseases and conditions disclosed herein including: asthma, cough, and bronchitis.

16 Claims, No Drawings

HETEROCYCLIC SUBSTITUTED PYRROLIDINE AMIDE DERIVATIVES

This application claims the benefit of U.S. provisional application No. 60/067,213, filed Dec. 19, 1996.

The present invention relates to novel heterocyclic substituted pyrrolidine amide derivatives (herein referred to as compounds or compounds of formula (1)), and stereoisomers thereof, and pharmaceutically acceptable salts thereof and their use as tachykinin receptor antagonists. Such antagonists are useful in the treatment of tachykinin-mediated diseases and conditions disclosed herein including: asthma, cough, and bronchitis.

BACKGROUND OF THE INVENTION

Certain substituted pyrrolidine derivatives are known to be tachykinin receptor antagonists. We have surprisingly found that the heterocyclic substituted pyrrolidine amide derivatives of the present invention are much less metabolized than the known compounds.

SUMMARY OF THE INVENTION

The present invention relates to novel heterocyclic substituted pyrrolidine amide derivatives of formula (1):

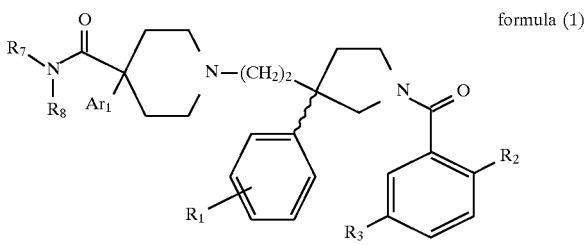

formula (1)

wherein $R_1$ is from 1 to 3 substituents each independently chosen from the group consisting of hydrogen, halogen, —$CF_3$, $C_1$–$C_6$ alkyl, and $C_1$–$C_6$ alkoxy;

$R_2$ is from chosen from the group consisting of hydrogen, $C_1$–$C_4$ alkyl, and $C_1$–$C_4$ alkoxy;

$R_3$ is a radical selected from the group consisting of

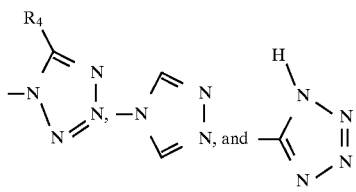

wherein $R_4$ is selected from the group consisting of hydrogen, $C_1$–$C_4$ alkyl, and —$CF_3$;

$Ar_1$ is a radical selected from the group consisting of

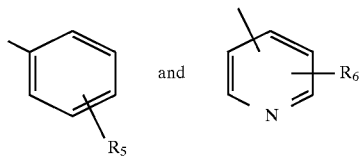

wherein $R_5$ is from 1 to 3 substituents each independently chosen from the group consisting of hydrogen, halogen, —$CF_3$, $C_1$–$C_6$ alkyl, and $C_1$–$C_6$ alkoxy;

$R_6$ is from 1 to 2 substituents each independently chosen from the group consisting of hydrogen, halogen, $C_1$–$C_6$ alkyl, and $C_1$–$C_6$ alkoxy;

$R_7$ and $R_8$ are hydrogen or together with the nitrogen to which they are attached form a piperidine, morpholine, piperazine, 4-methylpiperazine, or pyrrolidine ring;

and stereoisomers, and pharmaceutically acceptable salts thereof.

As is appreciated by one of ordinary skill in the art the compounds of the formula (1) exist as stereoisomers. Any reference in this application to one of the compounds of the formula (1) is meant to encompass either specific stereoisomers or a mixture of stereoisomers. Where indicated, the compounds follow the (+)- and (−)- designation or the Cahn-Ingold-Prelog designation of (R)- and (S)- for the stereochemistry of compounds represented by formula (1) and intermediates thereof. It is specifically recognized that the novel heterocyclic substituted pyrrolidine amide derivatives of the present invention are asymmetric in the 3-position of the pyrrolidine and may exist in the (R)- or (S)-configuration or may be a mixture thereof.

The specific stereoisomers can be prepared by stereospecific synthesis using enantiomerically pure or enantiomerically enriched starting materials. The specific stereoisomers of either starting materials or products can be resolved and recovered by techniques known in the art, such as chromatography on chiral stationary phases, enzymatic resolution, or fractional recrystallization of addition salts formed by reagents used for that purpose. Useful methods of resolving and recovering specific stereoisomers are know in the art and described in *Stereochemistry of Organic Compounds*, E. L. Eliel and S. H. Wilen, Wiley (1994) and *Enantiomers, Racemates, and Resolutions*, J. Jacques, A. Collet, and S. H. Wilen, Wiley (1981).

As is readily apparent to those skilled in the art some of the compounds of formula (1) may exists as tautomers. Any reference in this application to one of the tautomers of compounds of the formula (1) is meant to encompass every tautomeric form and mixtures thereof.

As used in this application:

a) the term "halogen" refers to a fluorine atom, chlorine atom, bromine atom, or iodine atom;

b) the term "$C_1$–$C_6$ alkyl" refers to a branched or straight chained alkyl radical containing from 1 to 6 carbon atoms, such as methyl, ethyl, n-propyl, isopropyl, n-butyl, isobutyl, sec butyl, t-butyl, pentyl, hexyl, etc;

c) the term "$C_1$–$C_4$ alkyl" refers to a branched or straight chained alkyl radical containing from 1 to 4 carbon atoms, such as methyl, ethyl, n-propyl, isopropyl, n-butyl, isobutyl, sec-butyl, t-butyl, etc;

d) the term "$C_1$–$C_6$ alkoxy" refers to a straight or branched alkoxy group containing from 1 to 6 carbon atoms, such as methoxy, ethoxy, n-propoxy, isopropoxy, n-butoxy, isobutoxy, sec-butoxy, t-butoxy, pentoxy, hexoxy, etc;

e) the term "$C_1$–$C_4$ alkoxy" refers to a straight or branched alkoxy group containing from 1 to 4 carbon atoms, such as methoxy, ethoxy, n-propoxy, isopropoxy, n-butoxy, isobutoxy, sec-butoxy, t-butoxy, etc;

f) the designation " ⌇ " refers to a bond for which the stereochemistry is not designated;

g) the designation " ▬ " refers to a bond that protrudes forward out of the plane of the page;

h) the designation " ▬ " refers to a bond that protrudes backward out of the plane of the page;

i) as used in the preparations and examples the following terms have the indicated meanings; "ng" refers to nanograms; "µg" refers to micrograms; "mg" refers to milligrams; "g" refers to grams; "kg" refers to kilograms; "nmole" or "inmol" refers to nanomoles; "mmol" refers to millimoles; "mol" refers to moles; "µL" refers to microliters; "mL" refers to milliliters; "L" refers to liters; "$R_f$" refers to retention factor; "° C." refers to degrees Celsius; "bp" refers to boiling point; "mm of Hg" refers to pressure in millimeters of mercury; "mp" refers to melting point; "dec" refers to decomposition; "$[\alpha]^2{}_D{}^0$" refer to specific rotation of the D line of sodium at 20° C. obtained in a 1 decimeter cell; "c" refers to concentration in g/mL; "nM" refers to nanomolar; "µM" refers to micromolar; "mM" refers to millimolar; "M" refers to molar; "psi" refers to pounds per square inch; "rpm" refers to revolutions per minute; "HPLC" refers to high performance liquid chromatography; "HRMS" refers to high resolution mass spectrum; "THF" refers to tetrahydrofuran; "brine" refers to a saturated aqueous solution of sodium chloride; "L.O.D." refers to loss on drying; "µCi" refers to microcuries; "i.p." refers to intraperitoneally; "i.v." refers to intravenously; and "DPM" refers to disintegrations per minute;

j) by the designation

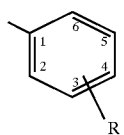

it is understood that the radical is attached at the 1-position and the substituent or substituents represented by R can be attached in any of the 2, 3, 4, 5, or 6 positions;

k) the designation

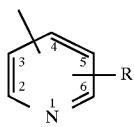

refers to a pyridyl or substituted pyridyl and it is understood that the radical can be attached at either the 2-position, the 3-position, or the 4-position, it is further understood that when the radical is attached at the 2-position the substituent or substituents represented by R can be attached in any of the 3, 4, 5, or 6 positions, that when the radical is attached at the 3-position the substituent or substituents represented by R can be attached in any of the 2, 4, 5, or 6 positions, and that when the radical is attached at the 4-position the substituent or substituents represented by R can be attached in any of the 2, 3, 5, or 6 positions;

l) the term "enantiomeric excess" or "ee" refers to the percent by which one enantiomer, E1, is in excess in a mixture of the two enantiomers, E1 plus E2, such that $$\{(E1-E2) \div (E1+E2)\} \times 100$$

=ee;

m) the term "pharmaceutically acceptable salts thereof" refers to either an acid addition salt or a basic addition salt.

The expression "pharmaceutically acceptable acid addition salts" is intended to apply to any non-toxic organic or inorganic acid addition salt of the base compounds represented by formula (1). Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzo.ic, p-toluenesulfonic acid, and sulfonic acids such as benzenesulfonic acid, methanesulfonic acid, and 2-hydroxyethanesulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by formula (1). Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

As with any group of structurally related compounds which possesses a particular utility, certain groups and configurations are preferred for the compounds of formula (1) in their end-use application.

Preferred embodiments of formula (1) are given below:

1) Compounds in which $R_2$ is methoxy are preferred;
2) Compounds in which $R_1$ is 3,4-dichloro are preferred;
3) Compounds in which $R_3$ is a radical selected from the group

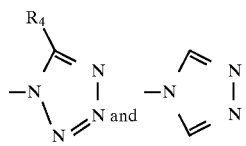

wherein $R_4$ is as defined above, are preferred;

4) Compounds in which $R_3$ is the radical

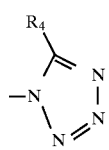

wherein $R_4$ is as defined above, are more preferred;

5) Compounds in which $R_7$ and $R_8$ are hydrogen are preferred.

It is understood that further preferred embodiments of formula (1) can be selected by requiring one or more of the preferred embodiments 1 through 5 of formula (1) or by reference to examples given herein.

Illustrative of compounds encompassed by the present invention include the following. It is understood that the examples encompass both the (R)-isomers and the (S)-isomers of the compound at both the 3-position of the pyrrolidine and mixtures thereof. This list is meant to be representative only and is not intended to limit the scope of the invention in any way:

1-(2-methoxy-5-(1H-tetrazol-1-yl)benzoyl)-3-(2-(4-phenyl-4-carboxamidopiperidin-1-yl)ethyl)-3-(:3,4-dimethoxyphenyl)pyrrolidine;

1-(2-methoxy-5-(1H-tetrazol-1-yl)benzoyl)-3-(2-(4-phenyl-4-carboxamidopiperidin-1-yl)ethyl)-3-(3-methoxyphenyl)pyrrolidine;

1-(2-methoxy-5-(1H-tetrazol-1-yl)benzoyl)-3-(2-(4-phenyl-4-carboxamidopiperidin-1-yl)ethyl)-3-(3,4-dichlorophenyl)pyrrolidine;

1-(2-methoxy-5-(1H-tetrazol-1-yl)benzoyl)-3-(2-(4-phenyl-4-carboxamidopiperidin-1-yl)ethyl)-3-(3-chlorophenyl) pyrrolidine;

1-(2-methoxy-5-(1H-tetrazol-1-yl)benzoyl)-3-(2-(4-phenyl-4-carboxamidopiperidin-1-yl)ethyl)-3-(3,4-difluorophenyl)pyrrolidine;

1-(2-methoxy-5-(1H-tetrazol-1-yl)benzoyl)-3-(2-(4-phenyl-4-carboxamidopiperidin-1-yl)ethyl)-3-(3-fluorophenyl) pyrrolidine;

1-(2-methoxy-5-(1H-tetrazol-1-yl)benzoyl)-3-(2-(4-phenyl-4-carboxamidopiperidin-1-yl)ethyl)-3-(4-fluorophenyl) pyrrolidine;

1-(2-methoxy-5-(1H-tetrazol-1-yl)benzoyl)-3-(2-(4-phenyl-4-carboxamidopiperidin-1-yl)ethyl)-3-(3,4-dimethylphenyl)pyrrolidine;

1-(2-methoxy-5-(1H-tetrazol-1-yl)benzoyl)-3-(2-(4-phenyl-4-carboxamidopiperidin-1-yl)ethyl)-3-phenylpyrrolidine;

1-(2-methoxy-5-(1H-tetrazol-1-yl)benzoyl)-3-(2-(4-phenyl-4-carboxamidopiperidin-1-yl)ethyl)-3-(4-trifluormethylphenyl)pyrrolidine;

1-(2-methoxy-5-(1H-tetrazol-1-yl)benzoyl)-3-(2-(4-(pyrid-3-yl)-4-carboxamidopiperidin-1-yl)ethyl)-3-(3,4-methoxyphenyl)pyrrolidine;

1-(2-methoxy-5-(1H-tetrazol-1-yl)benzoyl)-3-(2-(4-(pyrid-3-yl)-4-carboxamidopiperidin-1-yl)ethyl)-3-(3-methoxyphenyl)pyrrolidine;

1-(2-methoxy-5-(1H-tetrazol-1-yl)benzoyl)-3-(2-(4-(pyrid-3-yl)-4-carboxamidopiperidin-1-yl)ethyl)-3-(3,4-dichlorophenyl)pyrrolidine;

1-(2-methoxy-5-(1H-tetrazol-1-yl)benzoyl)-3-(2-(4-(pyrid-3-yl)-4-carboxamidopiperidin-1-yl)ethyl)-3-(3-chlorophenyl)pyrrolidine;

1-(2-methoxy-5-(1H-tetrazol-1-yl)benzoyl)-3-(2-(4-(pyrid-3-yl)-4-carboxamidopiperidin-1-yl)ethyl)-3-(3,4-difluorophenyl)pyrrolidine; 1-(2-methoxy-5-(1H-tetrazol-1-yl)benzoyl)-3-(2-(4-(pyrid-3-yl)-4-carboxamidopiperidin-1-yl)ethyl)-3-(3-fluorophenyl) pyrrolidine;

1-(2-methoxy-5-(1H-tetrazol-1-yl)benzoyl)-3-(2-(4-(pyrid-3-yl)-4-carboxamidopiperidin-1-yl)ethyl)-3-(4-fluorophenyl)pyrrolidine;

1-(2-methoxy-5-(1H-tetrazol-1-yl)benzoyl)-3-(2-(4-(pyrid-3-yl)-4-carboxamidopiperidin-1-yl)ethyl)-3-(3,4-dimethylphenyl)pyrrolidine;

1-(2-methoxy-5-(1H-tetrazol-1-yl)benzoyl)-3-(2-(4-(pyrid-3-yl)-4-carboxamidopiperidin-1-yl)ethyl)-3-phenylpyrrolidine; 1-(2-methoxy-5-(1H-tetrazol-1-yl)benzoyl)-3-(2-(4-(Pyrid-2-yl)-4-carboxamidopiperidin-1-yl)ethyl)-3-(3,4-methoxyphenyl)pyrrolidine;

1-(2-methoxy-5-(1H-tetrazol-1-yl)benzoyl)-3-(2-(4-(pyrid-2-yl)-4-carboxamidopiperidin-1-yl)ethyl)-3-(3-methoxyphenyl)pyrrolidine;

1-(2-methoxy-5-(1H-tetrazol-1-yl)benzoyl)-3-(2-(4-(pyrid-2-yl)-4-carboxamidopiperidin-1-yl)ethyl)-1)-3-(3,4-dichlorophenyl)pyrrolidine;

1-(2-methoxy-5-(1H-tetrazol-1-yl)benzoyl)-3-(2-(4-(pyrid-2-yl)-4-carboxamidopiperidin-1-yl)ethyl)-3-(3-chlorophenyl)pyrrolidine;

1-(2-methoxy-5-(1H-tetrazol-1-yl)benzoyl)-3-(2-(4-(pyrid-2-yl)-4-carboxamidopiperidin-1-yl)ethyl)-3-(3,4-difluorophenyl)pyrrolidine;

1-(2-methoxy-5-(1H-tetrazol-1-yl)benzoyl)-3-(2-(4-(pyrid-2-yl)-4-carboxamidopiperidin-1-yl)ethyl)-3-(3-fluorophenyl)pyrrolidine;

1-(2-methoxy-5-(1H-tetrazol-1-yl)benzoyl)-3-(2-(4-(pyrid-2-yl)-4-carboxamidopiperidin-1-yl)ethyl)-3-(4-fluorophenyl)pyrrolidine;

1-(2-methoxy-5-(1H-tetrazol-1-yl)benzoyl)-3-(2-(4-(pyrid-2-yl)-4-carboxamidopiperidin-1-yl)ethyl)-3-(3,4-dimethylphenyl)pyrrolidine;

1-(2-methoxy-5-(1H-tetrazol-1-yl)benzoyl)-3-(2-(4-(pyrid-2-yl)-4-carboxamidopiperidin-1-yl)ethyl)-3-phenylpyrrolidine;

1-(2-methoxy-5-(1H-tetrazol-1-yl)benzoyl)-3-(2-(4-(pyrid-4-yl)-4-carboxamidopiperidin-1-yl)ethyl)-3-(3,4-methoxyphenyl)pyrrolidine;

1-(2-methoxy-5-(1H-tetrazol-1-yl)benzoyl)-3-(2-(4-(pyrid-4-yl)-4-carboxamidopiperidin-1-yl)ethyl)-3-(3-methoxyphenyl)pyrrolidine;

1-(2-methoxy-5-(1H-tetrazol-1-yl)benzoyl)-3-(2-(4-(pyrid-4-yl)-4-carboxamidopiperidin-1-yl)ethyl)-3-(3,4-dichlorophenyl)pyrrolidine;

1-(2-methoxy-5-(1H-tetrazol-1-yl)benzoyl)-3-(2-(4-(pyrid-4-yl)-4-carboxamidopiperidin-1-yl)ethyL)-3-(3-chlorophenyl)pyrrolidine;

1-(2-methoxy-5-(1H-tetrazol-1-yl)benzoyl)-3-(2-(4-(pyrid-4-yl)-4-carboxamidopiperidin-1-yl)ethyl)-3-(3,4-difluorophenyl)pyrrolidine; 1-(2-methoxy-5-(1H-tetrazol-1-yl)benzoyl)-3-(2-(4-(pyrid-4-yl)-4-carboxamidopiperidin-1-yl)ethyl)-3-(3-fluorophenyl) pyrrolidine;

1-(2-methoxy-5-(1H-tetrazol-1-yl)benzoyl)-3-(2-(4-(pyrid-4-yl)-4-carboxamidopiperidin-1-yl)ethyl)-3-(4-fluorophenyl)pyrrolidine;

1-(2-methoxy-5-(1H-tetrazol-1-yl)benzoyl)-3-(2-(4-(pyrid-4-yl)-4-carboxamidopiperidin-1-yl)ethyl)-3-(3,4-dimethylphenyl)pyrrolidine;

1-(2-methoxy-5-(1H-tetrazol-1-yl)benzoyl)-3-(2-(4-(pyrid-4-yl)-4-carboxamidopiperidin-1-yl)ethyl)-3-phenylpyrrolidine;

1-(2-methoxy-5-(5-methyl-1H-tetrazol-1-yl)benzoyl)-3-(2-(4-phenyl-4-carboxamidopiperidin-1-yl)elhyl)-3-(3,4-dichlorophenyl)pyrrolidine;

1-(2-methoxy-5-(5-trifluoromethyl-1H-tetrazol-1-yl) benzoyl)-3-(2-(4-phenyl-4-carboxamidopiperidin-1-yl) ethyl)-3-(3,4-dichlorophenyl)pyrrolidine;

1-(2-methoxy-5-(4H-triazol-4-yl)benzoyl)-3-(2-(4-phenyl-4-carboxamidopiperidin-1-yl)ethyl)-3-(3,4-dichlorophenyl)pyrrolidine;

1-(3-(1H-tetrazol-1-yl)benzoyl)-3-(2-(4-phenyl-4-carboxamidopiperidin-1-yl)ethyl)-3-(3,4-dichlorophenyl) pyrrolidine;

1-(2-methyl-5-(1H-tetrazol-1-yl)benzoyl)-3-(2-(4-phenyl-4-carboxamidopiperidin-1-yl)ethyl)-3-(3,4-dichlorophenyl) pyrrolidine;

1-(2-methoxy-5-(1H-tetrazol-5-yl)benzoyl)-3-(2-(4-phenyl-4-carboxamidopiperidin-1-yl)ethyl)-3-(3,4-dichlorophenyl)pyrrolidine;

1-(2-methoxy-5-(1H-tetrazol-1-yl)benzoyl)-3-(2-(4-phenyl-4-(morpholin-4-ylcarboxamido)piperidin-1-yl)ethyl)-3-(3,4-dichlorophenyl)pyrrolidine;

1-(2-methoxy-5-(1H-tetrazol-1-yl)benzoyl)-3-(2-(4-phenyl-4-(pyrrolidin-1-ylcarboxamido)piperidin-1-yl)ethyl)-3-(3,4-dichlorophenyl)pyrrolidine;

1-(2-methoxy-5-(1H-tetrazol-1-yl)benzoyl)-3-(2-(4-phenyl-4-(piperidin-1-ylcarboxamido)piperidin-1-yl)ethyl)-3-(3,4-dichlorophenyl)pyrrolidine;

1-(2-methoxy-5-(1H-tetrazol-1-yl)benzoyl)-3-(2-(4-phenyl-4-(piperazin-1-ylcarboxamido)piperidin-1-yl)ethyl)-3-(3,4-dichlorophenyl)pyrrolidine;

1-(2-methoxy-5-(1H-tetrazol-1-yl)benzoyl)-3-(2-(4-phenyl-4-(4-methylpiperazin-1-ylcarboxamido)piperidin-1-yl)ethyl)-3-(3,4-dichlorophenyl)pyrrolidine.

General synthetic procedures are set forth in Reaction Schemes A.1 and A.2 for preparing these compounds of formula (1). The reagents and starting materials are readily available to one of ordinary skill in the art. In Reaction Schemes A.1 and A.2, all substituents, unless otherwise indicated, are as previously defined.

mesylate being preferred. The conversion of hydroxy groups to leaving groups such as chloro, bromo, iodo, mesylate, and tosylate is well known and appreciated in the art.

For example, compounds in which $L_1$ is bromo are formed by contacting an appropriate 3-(2-hydroxyethyl)pyrrolidine of formula 2 with 1.0 to 1.5 molar equivalents of carbot tetrabromide and 1.0 to 1.75 molar equivalents triphenylphosphine. (P. J. Kocienski et al. *J. Org. Chem.*, 42, 353–355 (1977)). The reaction is carried out by combining the 3-(2-hydroxyethyl)pyrrolidine of formula 2 with carbon tetrabromide in a suitable solvent, such as dichloromethane or chloroform and then adding a solution of triphenylphosphine in a suitable solvent, such as dichloromethane or chloroform. Generally the reaction is carried out at temperatures of from −10° C. to ambient temperature. Generally, the

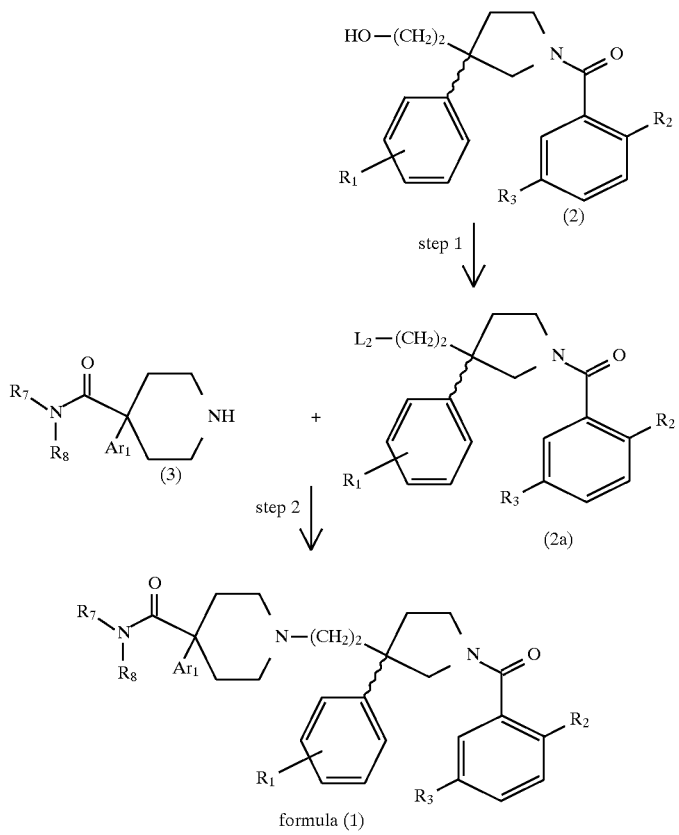

Reaction Scheme A.1

In Reaction Scheme A.1, step 1, the hydroxy group of an appropriate 3-(2-hydroxyethyl)pyrrolidine of formula 2 is converted to an appropriate leaving group, $L_1$, to give a 3-(2-$L_1$-ethyl)pyrrolidine of formula 2a. An appropriate 3-(2-hydroxyethyl)pyrrolidine of formula 2 is one in which $R_1$, $R_2$, and $R_3$ are as desired in the final product of formula (1). An appropriate 3-(2-hydroxyethyl)pyrrolidine of formula 2 may also have the stereochemistry as desired in the final product of formula (1). Appropriate compounds of formula 2 can be prepared as described herein and as described in U.S. Pat. No. 5,340,822 and PCT WO 94/26735. An appropriate leaving group, $L_1$, is one which can be displaced by a piperidine of formula 3 to give a compound of formula (1) or protected compound of formula (1). Appropriate leaving groups include but are not limited to chloro, bromo, iodo, mesylate, tosylate, and the like, with reactions require from 5 minutes to 24 hours. The product can be isolated and purified by techniques well known in the art, such as extraction, evaporation, trituration, chromatography, and recrystallization.

Compounds in which $L_1$ is bromo are also formed by contacting an appropriate 3-(2-hydroxyethyl)pyrrolidine of formula 2 with a slight molar excess of triphenylphosphine dibromide. (R. F Borch et al. *J. Am. Chem. Soc.*, 99, 1612–1619 (1977)). The reaction is carried out in a suitable solvent, such as tetrahydrofuran and diethyl ether. The reaction is carried out in the presence of a suitable base, such as pyridine. Generally the reaction is carried out at temperatures of from 0° C. to 50° C. Generally, the reactions require from 5 minutes to 24 hours. The product can be isolated and purified by techniques well known in the art, such as extraction, evaporation, trit:uration, chromatography, and recrystallization.

Compounds in which $L_1$ is mesylate are formed by contacting an appropriate 3-(2-hydroxyethyl)pyrrolidine of formula 2 with 1 to 2 molar equivalents of methanesulfonyl chloride. The reaction is carried out in a suitable substantially anhydrous solvent, such as dichloromethane, chloroform, toluene, benzene, or pyridine. The reaction is carried out in the presence of from 1 to 5 molar equivalents of a suitable base, such as triethylamine, N,N-diisopropylethylamine, N-methylmorpholine, or pyridine. Generally the reaction is carried out at temperatures of from −20° C. to 50° C. Generally, the reactions require from 1 hour to 24 hours. The product can be isolated and purified by techniques well known in the art, such as extraction, evaporation, trituration, chromatography, and recrystallization.

Compounds of formula 2a in which $L_1$ is iodo can be prepared from compounds of formula 2a in which $L_1$ is mesylate, chloro, or bromo by an exchange reaction, such as the Finkelstein reaction.

For example, a compound of formula 2a in which $L_1$ is mesylate, chloro, or bromo is contacted with from 1.0 to 10.0 molar equivalents of an iodide salt, such as sodium iodide or potassium iodide. The reaction is carried out in a suitable solvent, such as acetone or butanone. Generally, the reaction is carried out at temperatures of from ambient temperature to the refluxing temperature of the solvent. Generally, the reactions require from 1 hour to 24 hours. The product can be isolated and purified by techniques well known in the art, such as extraction, evaporation, trituration, chromatography, and recrystallization.

In Reaction Scheme A.1, step 2, an appropriate 3-(2-$L_1$-ethyl)pyrrolidine of formula 2a reacts with an appropriate piperidine compound of formula 3 or salt thereof to give a protected compound of formula (1). Akn appropriate piperidine compound of formula 3 is one in which $Ar_1$, $R_7$, and $R_8$ are as desired in the final product of formula (1).

For example, an appropriate 3-(2-$L_1$-ethyl)pyrrolidine of formula 2a is contacted with an appropriate piperidine compound of formula 3 or salt thereof to give a compound of formula (1). The reaction is carried out in a suitable substantially anhydrous solvent, such as tetrahydrofuran, pyridine, acetonitrile, toluene, or dimethylformamide using from 1.0 to 6.0 molar equivalents of a suitable base, such as triethylamine, pyridine, or N,N-diisopropylethylamine. When a salt of an appropriate piperidline of formula 3 is used, an additional molar equivalent of a suitable base is used. The reaction may be facilitated by the addition of a catalytic amount, 0.1 to 0.5 molar equivalents, of an iodide salt, such as sodium iodide or potassium iodide. The reaction is generally carried out at temperatures of from ambient temperature to the refluxing temperature of the solvent. Generally, the reactions require 1 to 72 hours. The product can be isolated and purified by techniques well known in the art, such as extraction, evaporation, trituration, chromatography, and recrystallization.

Alternately, the reaction is carried out in a suitable mixed solvent, such as toluene/water mixtures, ethyl acetate/water mixtures, or tetrahydrofuran/water mixtures, using from 1.0 to 6.0 molar equivalents of a suitable base, such as sodium hydroxide, potassium hydroxide, sodium carbonate, sodium bicarbonate, potassium carbonate, or potassium bicarbonate. As above, when a salt of an appropriate piperidine of formula 3 is used, an additional molar equivalent of a suitable base is used. The reaction may be facilitated by the addition of a catalytic amount, 0.1 to 0.5 molar equivalents, of an iodide salt, such as sodium iodide or potassium iodide. The reaction is generally carried out at temperatures of from ambient temperature to the refluxing temperature of the mixed solvent. Generally, the reactions require 1 to 150 hours. The product can be isolated and purified by techniques well known in the art, such as extraction, evaporation, trituration, chromatography, and recrystallization.

In addition, pharmaceutically acceptable salts of a compound of formula (1) are readily prepared from compounds of formula (1) by methods and techniques well known and appreciated in the art.

Reaction Scheme A.2

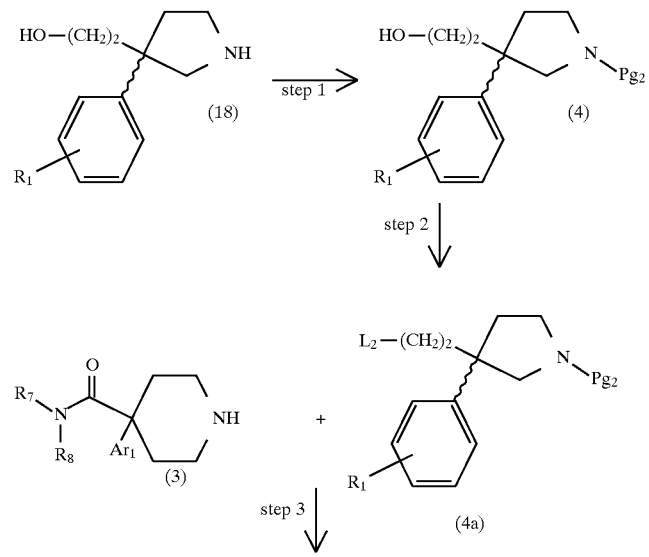

-continued
Reaction Scheme A.2

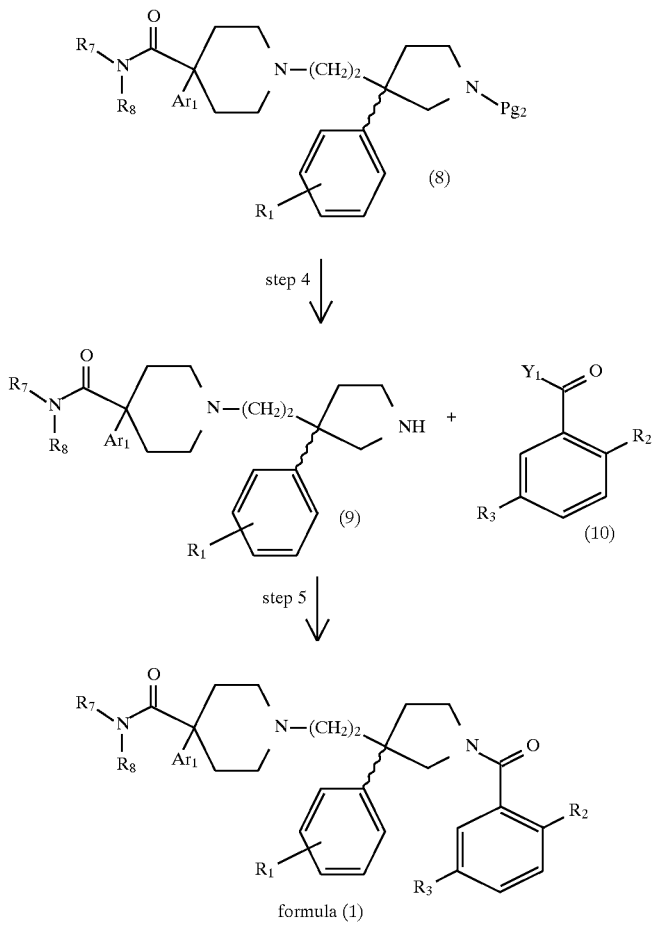

formula (1)

In Reaction Scheme A.2, step 1, the amine function of an appropriate 3-(2-hydroxyethyl)pyrrolidine of structure 18 is protected to give a protected 3-(2-hydroxyethyl)pyrrolidine of structure 4. An appropriate 3-(2-hydroxyethyl) pyrrolidine of formula 18 is one in which $R_1$ is as desired in the final product of formula (1). An appropriate 3-(2-hydroxyethyl)pyrrolidine of formula 18 may also have the stereochemistry as desired in the final product of formula (1). The selection and use of suitable amine protecting groups is described in *Protecting Groups in Organic Synthesis* by T. Greene is well known and appreciated in the art. In Scheme A.2, step 1, the use of carbamate protecting groups, such as t-butoxycarbonyl is preferred.

In Reaction Scheme A.2, step 2, the hydroxy group of a protected 3-(2-hydroxyethyl)pyrrolidine of structure 4 is converted to an appropriate leaving group, $L_2$, as taught in Reaction Scheme A.1, step 1 for the conversion of hydroxy groups to the leaving group $L_1$, to give of a 3-(2-$L_2$-ethyl) pyrrolidine of formula 4a. In Reaction Scheme A.2, step 2, an appropriate leaving group, $L_2$, include chloro, bromo, iodo, and mesylate.

In Reaction Scheme A.2, step 3, an 3-(2-$L_2$-ethyl) pyrrolidine of formula 4a reacts with an appropriate piperidine compound of formula 3 or salt thereof, as taught in Reaction Scheme A.1, step 2, to give a protected 3-(2-(piperidin-1-yl)ethyl)pyrrolidine of structure 8. An appropriate piperidine compound of formula 3 is as described in Reaction Scheme A.1, step 2.

In Reaction Scheme A.2, step 4, a protected 3-(2-(piperidin-1-yl)ethyl)pyrrolidine of structure 8 is deprotected to give a 3-(2-(piperidin-1-yl)ethyl)pyrrolidine of structure 9 or salt thereof. The removal of suitable amine protecting groups as described in *Protecting Groups in Organic Synthesis* by T. Greene is well known and appreciated in the art.

In Reaction Scheme A.2, step 5, a 3-(2-(piperidin-1-yl) ethyl)pyrrolidine of structure 9 or salt thereof is aroylated by an appropriate acid derivative of structure 10 to give the final product of formula (1). An appropriate acid derivative of structure 10 is one in which $R_2$ and $R_3$ are as desired in the final product of formula (1) and $Y_1$ is hydroxyl; an activated ester, such as O-hydroxysuccinimide or O-hydroxybenztriazole; an activated leaving group, such as chloro, bromo; or another acid derivative of structure 10 to form an anhydride; or mixed anhydride.

For example, the 3-(2-(piperidin-1-yl)ethyl)pyrrolidine of structure 9 or salt thereof is contacted with O-hydroxysuccinimide or O-hydroxybenztriazole and a coupling reagent such as dicyclohexylcarbodiimide or 1-ethyl-3-(3-dimethylaminopropyl)carbodiimide hydrochloric acid salt and then with 0.9 to 1.3 molar equivalents of an appropriate acid derivative of structure 10 in which $Y_1$ is hydroxy. The reaction is carried out in a suitable solvent, such as dichloromethane or chloroform. The reaction is carried out in the presence of a base as needed, 1.0 to 1.1 equivalents being used for each, when the salt of the coupling agent or of the 3-(2-(piperidin-1-yl)ethyl) pyrrolidine of structure 9 is used. Suitable bases include, N-methylmorpholin.-, triethylamine, and N,N-diisopropylethylamine. The reaction is generally carried out at temperatures of from −10° C. to ambient temperature. Generally, the reactions require 1 to 24 hours. The product can be isolated and purified by techniques well known in the art, such as extraction, evaporation, trituration, chromatography, and recrystallization.

Also, for example, the 3-(2-(piperidin-1-yl)ethyl) pyrrolidine of structure 9 or salt thereof is contacted with 1 to 1.1 molar equivalents of an appropriate acid derivative of structure 10 as its halide, anhydride, or mixed anhydride. The reaction is carried out in a suitable solvent, such as tetrahydrofuran, dichloromethane, acetone, ethyl acetate, toluene, or diethyl ether. The reaction is carried out in the presence of a base, such as N-methylmorpholine, sodium carbonate, triethylamine, N,N-diisopropylethylamine, potassium carbonate or sodium bicarbonate. The reaction is generally carried out at temperatures of from −78° C. to ambient temperature. Generally, the reactions require 1 to 24 hours. The product can be isolated and purified by techniques well known in the art, such as extraction, evaporation, trituration, chromatography, and recrystallization.

Alternately, for example, the 3-(2-(piperidin-1-yl)ethyl) pyrrolidine of structure 9 or salt thereof is contacted with 1 to 1.1 molar equivalents of an appropriate acid derivative of structure 10 as its halide, anhydride, or mixed anhydride under Schotten-Baumann conditions. The reaction is carried out in a suitable solvent mixture, such as toluene/water, acetone/water, tetrahydrofuran/water, or ethyl acetate/water. The reaction is carried out in the presence of a base, such as potassium carbonate, potassium bicarbonate, sodium bicarbonate, sodium carbonate, sodium hydroxide, or potassium hydroxide. The reaction is generally carried out at temperatures of from −20° C. to 50° C. Generally, the reactions require 15 minutes to 24 hours. The product can be isolated and purified by techniques well known in the art, such as extraction, evaporation, trituration, chromatography, and recrystallization.

In addition, pharmaceutically acceptable salts of a compound of formula (1) are readily prepared from compounds of formula (1) by methods and techniques well known and appreciated in the art.

Reaction Scheme B is a general scheme for preparing alcohols of structure 2 used as a starting material in Reaction Scheme A.1 and 3-(2-hydroxyethyl)pyrrolidine of structure 18 used as a starting material in Reaction Scheme A.2. The reagents and starting materials are readily available to one of ordinary skill in the art. In Reaction Scheme B, all substituents, unless otherwise indicated, are as previously defined.

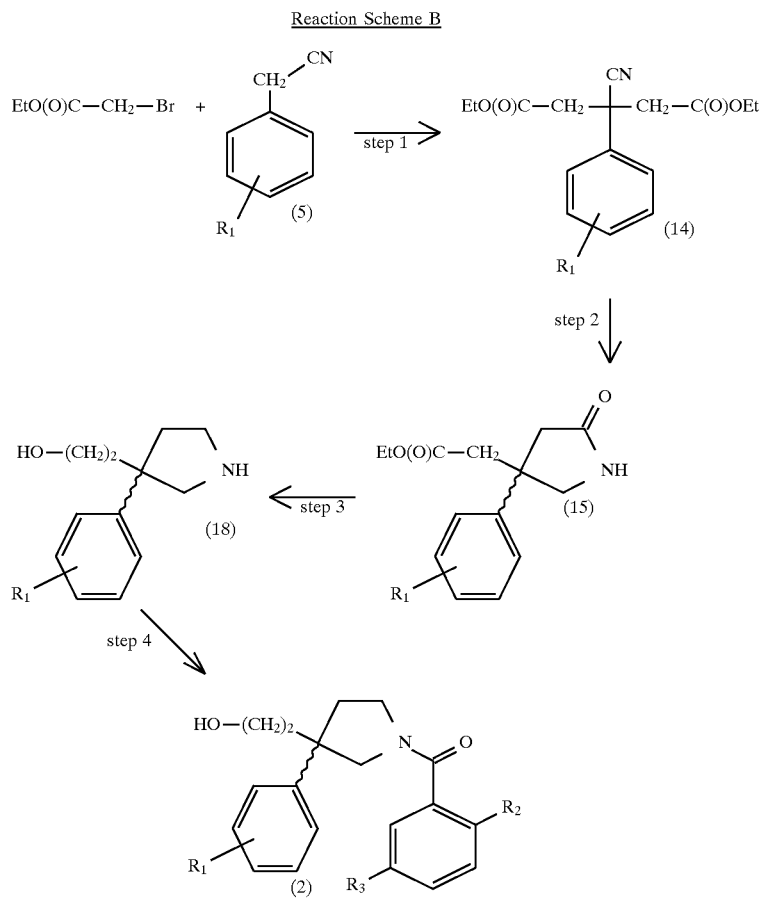

Reaction Scheme B

In Reaction Scheme B, step 1, an appropriate nitrile of structure 5 is bis-alkylated with ethyl bromoacetate to give a nitrile bis-ester compound of structure 14. An appropriate nitrile of structure 5 is one in which $R_1$ is as desired in the final product of formula (1).

For example, an appropriate nitrile of structure 5 is contacted with 2.0 to 3.0 molar equivalents of ethyl bromoacetate. The reaction is carried out in the presence of approximately 2.0 to 3.0 molar equivalents of a suitable base, such as sodium bis(trimethylsilyl)amide or lithium diisopropylamide. The reaction is carried out in a suitable solvent, such as tetrahydrofuran. The reaction is generally carried out at temperatures of from −78° C to 0° C. Generally, the reactions require 1 to 72 hours. The product can be isolated and purified by techniques well known in the art, such as extraction, evaporation, trituration, distillation, chromatography, and recrystallization.

In Reaction Scheme B, step 2, the nitrile bis-ester compound of structure 14 is reduced and cyclized to give a 5-oxo-3-acetic acid ester pyrrolidine of structure 15. The cyclization may occur spontaneously after the reduction or may be carried out in a separate step after the isolation of the intermediate amine.

For example, the nitrile ester compound of structure 14 is contacted with an excess of an appropriate reducing agent, such as sodium borohydride in the presence of cobalt (II) chloride hexahydrate; hydrogen in the presence of a suitable catalyst, such as Raney nickel or platinum oxide; or a borane complex, such as borane dimethylsulfide complex.

When sodium borohydride in the presence of cobalt chloride is used, the reaction is carried out in a suitable solvent, such as methanol, or ethanol. The reaction is generally carried out at temperatures of from 0° C. to 50° C. Generally, the reactions require 1 to 72 hours. Generally, the cyclization occurs spontaneously under these conditions. The product can be isolated and purified by techniques well known in the art, such as extraction with aqueous acid, evaporation, trituraticon, chromatography, and recrystallization.

When Raney nickel is used, the reaction is carried out in a suitable solvent containing ammonia, such as ethanol/aqueous ammonium hydroxide or methanol/aqueous ammonium hydroxide. The reaction is generally carried out at temperatures of from ambient temperature to 70° C. The reaction is carried out with hydrogen at pressures of from 15 psi to 300 psi in an apparatus designed for carrying out reactions under pressure, such as a Parr hydrogenation apparatus. Generally, the cyclization occurs spontaneously under these conditions. The product can be isolated by carefully removing the catalyst by filtration and evaporation. The product can be purified by extraction, evaporation, trituration, chromatography, and recrystallization.

When platinum oxide is used, the reaction is carried out in a suitable solvent such as ethanol, methanol, chloroform, ethanol/chloroform mixtures, or methanol/chloroform mixtures. The reaction is generally carried out at temperatures of from ambient temperature to 50° C. The reaction is carried out with hydrogen at pressures of from 15 psi to 120 psi in an apparatus designed for carrying out reactions under pressure, such as a Parr hydrogenation apparatus. Generally, an amine intermediate is obtained under these conditions and is isolated by carefully removing the catalyst by filtration and evaporation. The amine intermediate is cyclized by heating in a suitable solvent, such as ethanol, methanol, toluene, or chlorobenzene. The reaction is generally carried out at temperatures of from 50° C. to the refluxing temperature of the solvent. Generally, the reaction requires 8 to 48 hours. The product can be purified by extraction, evaporation, trituration, chromatography, and recrystallization.

Alternately, for example, the nitrile bis-ester compound of structure 14 is contacted with borane or a borane complex, such as borane dimethylsulfide complex. The reaction is carried out in a suitable solvent, such as diethyl ether or tetrahydrofuran. The reaction is generally carried out at temperatures of from −20° C. to the refluxing temperature of the solvent. Generally, the reactions require 1 to 72 hours. The product can be isolated and purified by techniques well known in the art, such as quenching, extraction, evaporation, trituration, distillation, chromatography, and recrystallization.

In Reaction Scheme B, step 3, the 5-oxo-3-acetic acid ester pyrrolidine of structure 15 is reduced to give a 3-(2-hydroxyethyl)pyrrolidine of structure 18.

For example, the 5-oxo-3-acetic acid ester pyrrolidine of structure 15 is contacted with an excess of a suitable reducing agent, such as lithium aluminum hydride, aluminum hydride, or borane dimethyl sulfide complex. A sufficient amount of reducing agent is used to reduce both the ester and amide functions. The reaction is carried out in a suitable solvent, such as tetrahydrofuran or diethyl ether. The reaction is generally carried out at temperatures of from 0° C. to the refluxing temperature of the solvent. Generally, the reactions require 1 to 72 hours. The product can be isolated and purified by techniques well known in the art, such as quenching of borane or aluminum complexes, extraction, evaporation, trituration, chromatography, and recrystallization.

In Reaction Scheme B, step 4, the 3-(2-hydroxyethyl) pyrrolidine of structure 18 is aroylated with an appropriate aroyl halide, aryl anhydride, or aryl mixed anhydride to give an alcohol of structure 2. An appropriate aryl acid, aryl ester, aroyl halide, aroyl anhydride, or aroyl mixed anhydride, $X_1$—C(O)—$Ph_1$, is one in which $Ph_1$ is substituted phenyl having $R_2$ and $R_3$ as desired in formula (1) and $X_1$ is hydroxyl; an activated ester, such as O-hydroxysuccinimide or O-hydroxybenztriazole esters; an activated leaving group, such as chloro, bromo; or a group —C(O)—$Ph_1$ which forms an anhydride; or a mixed anhydride.

For example, the 3-(2-hydroxyethyl)-pyrrolidine of structure 18 is contacted with 1 to 1.1 molar equivalents of an appropriate aroyl halide, aryl anhydride, or aryl mixed anhydride. The reaction is carried out in a suitable solvent, such as tetrahydrofuran, dichloromethane, acetone, ethyl acetate, toluene, or diethyl ether. The reaction is carried out in the presence of a base, such as N-methylmorpholine, sodium carbonate, triethylamine, N,N-diisopropylethylamine, potassium carbonate or sodium bicarbonate. The reaction is generally carried out at temperatures of from −78° C. to ambient temperature. Generally, the reactions require 1 to 24 hours. The product can be isolated and purified by techniques well known in the art, such as extraction, evaporation, trituration, chromatography, and recrystallization.

Alternately, for example, the 3-(2-hydroxyethyl)-pyrrolidine of structure 18 is contacted with 1 to 1.1 molar equivalents of an appropriate aroyl halide, aryl anhydride, or aryl mixed anhydride under Schotten-Baumann conditions. The reaction is carried out in a suitable solvent mixture, such as toluene/watier, acetone/water, tetrahydrofuran/water, or ethyl acetate/water. The reaction is carried out in the presence of a base, such as potassium carbonate, potassium bicarbonate, sodium bicarbonate, sodium carbonate, sodium hydroxide, or potassium hydroxide. The reaction is generally carried out at temperatures of from −20° C. to 50° C. Generally, the reactions require 15 minutes to 24 hours. The product can be isolated and purified by techniques well known in the art, such as extraction, evaporation, trituration, chromatography, and recrystallization.

Reaction Scheme C sets forth a synthetic procedure for preparing piperidine compounds of structure 3 used as starting materials in Reaction Schemes A.1 and A.2.

Reaction Scheme C

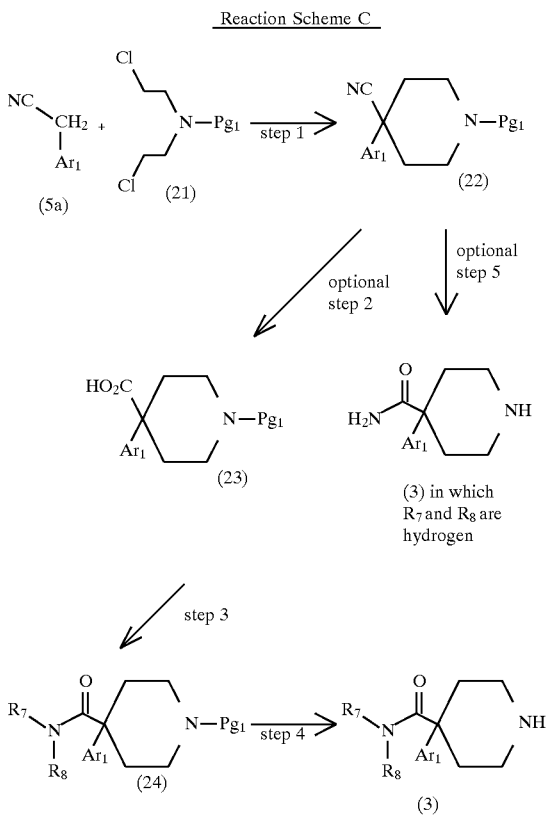

(3) in which R₇ and R₈ are hydrogen

In Reaction Scheme C, step 1, an appropriate protected bis-(2-chloroethyl)amine of formula 21 is alkylated with an appropriate arylacetonitrile of formula 5a to give a protected 4-aryl-4-cyanopiperidine of of formula 22. An appropriate protected bis-(2-chloroethyl)amine of formula 21 is one in which the protecting group, Pgl, may be $C_1$–$C_4$ alkyl, benzyl, substituted benzyl, p-toluenesulfonyl, benzenesulfonyl, or a carbamate, such as t-butoxycarbonyl or ethoxycarbonyl. An appropriate arylacetonitrile of formula 5a is one in which Arl is as desired in the final product of formula (1). Alkylation of this type are well known and appreciated in the art, some examples of which are found in T. Cammack and P. C. Reeves, *J. Heterocyclic Chem.* 23, 73–75 (1986) and C. V. Bercz and R. D. Ice, *J. Pharmaceutical Sci.*, 21, 1316–1317 (1972) among others.

For example, an appropriate protected bis-(2-chloroethyl) amine of formula 21 is contacted with an appropriate arylacetonitrile of formula 5a. The reaction is carried out in the presence of 2 to 4 molar equivalents a base, such as sodium amide, sodium hydride, sodium hexamethyldisilazide, potassium t-butoxide, and lithium diisopropylamide. The reaction is carried out in a solvent, such as dimethyl sulfoxide and tetrahydrofuran. The reaction can be carried out in the presence of 0.01 to 0.5 molar equivalents of a suitable catalyst, such as sodium iodide or potassium iodide. The reaction is generally carried out at temperatures of from 0° C. to 80° C. Generally, the reactions require 1 to 72 hours. The product can be isolated and purified by techniques well known in the art, such as extraction, evaporation, trituration, chromatography, and recrystallization.

Alternately, for example, an appropriate protected bis-(2-chloroethyl)amine of formula 21 is contacted with an appropriate arylacetonitrile of formula 5a under phase transfer conditions. The reaction may be carried out in water or in a solvent system consisting of an organic phase and an aqueous phase. The reaction is carried out in the presence of a hydroxide base, such as sodium hydroxide or potassium hydroxide. The reaction is carried out in the presence of a suitable catalyst including quaternary ammonium and phosphonium salts, such as tetrabutylammonium bromide, tetrabutylammonium hydrogen sulfate, hexadecyltributyl phosphonium bromide, benzyltrimethylammonium chloride, and the like. The reaction is vigorously stirred and is generally carried out at temperatures of between 0° C. and 100° C. Generally, the reactions require 1 to 24 hours. The product can be isolated and purified by techniques well known in the art, such as extraction, evaporation, trituration, chromatography, and recrystallization.

In Reaction Scheme C, optional step 2, a 4-aryl-4-cyanopiperidine of formula 22 is hydrolyzed to a 4-aryl-piperidine-4-carboxylic acid of formula 23. The hydrolysis of nitriles to acids may be carried out under acidic or basic conditions as is well known and appreciated in the art. The selection and use of hydrolysis conditions which are compatible with the protecting groups is well known and appreciated in the art. As appreciated by those skilled in the art, the removal of the amine protecting group, $Pg_1$, in either before or after step 2 may be required. For example, when $Pg_1$ is benzyl the protecting group may be removed to facilitate the hydrolysis of the nitrile and then reintroduced after hydrolysis. If removed, reintroduction of the protecting group either as benzyl or another protecting group, after hydrolysis gives a 4-aryl-piperidine-4-carboxylic acid of formula 23. Alternately, the protecting group used in Reaction Scheme C, steps 1 and 2, may be removed and replaced by another protecting group to facilitate deprotection of compound 24, in Reaction Scheme C, step 4. The removal and introduction of amine protecting groups is well known and appreciated in the art and taught in *Protecting Groups in Organic Synthesis* by T. Greene, Wiley-Interscience (1981).

In Reaction Scheme C, step 3, the 4-aryl-piperidine-4-carboxylic acid of formula 23 undergoes an amidation reaction with an appropriate amine to give a protected 4-aryl-4-carboxamido-piperidine of formula 24. An appropriate amine is one that gives the $R_7$ and $R_8$ as desired in the final product of formula (1). Such appropriate amines include, ammonia, piperidine, pyrrolidine, 4-methylpiperazine, piperazine, and morpholine.

An amidation reaction may proceed through the acid of formula 23 or the acid function of a compound of formula 23 may be first converted to an activated intermediate; such as an anhydride; a mixed anhydride of substituted phosphoric acid, such as dialkylphosphoric acid, diphenylphosphoric acid, halophosphoric acid; of aliphatic carboxylic acid, such as formic acid, acetic acid, propionic acid, butyric acid, isobutyric acid, pivalic acid, 2-ethylbutyric acidand the like; an activated ester, such as phenol ester, p-nitrophenol ester, N-hydroxysuccinimide ester, N-hydroxyplhthalimide ester, 1-hydroxybenztriazole ester, and the like; activated amide, such as imidazole, dimethylpyrazole, triazole, or tetrazole; or the intermediate formed in the presence of coupling agents, such as dicyclohexylcarbodiimide or 1-(3-dimethylaminopropyl)-3-ethylcarbodiirnide. Activated intermediates may be prepared and used directly, or are prepared and isolated before the addition of an appropriate carboxy substituted cyclic amine. Alternately, activated intermediates may be prepared isolated and purified before the addition of an appropriate carboxy substituted cyclic amine. The use and formation of activated intermediates is well known and appreciated in the art.

For example, an acid compound of formula 23 is contacted with a slight molar excess of an appropriate amine or a salt thereof and 1-hydroxybenzotriazole hydrate in the presence of a slight molar excess of a coupling agent, such as dicyclohexylcarbodiimide or 1-(3-dimethyaminopropyl)-3-thylcarbodiimide. The reaction is carried out in the presence of a suitable base, such as N,N-diisopropylethylamine, N-methylmorpholine, or triethylamine, and if the salt of an appropriate amine is used an additional molar amount of a suitable base is added. The reaction is carried out in a suitable solvent, such as dichloromethane, chloroform, or dimethylformamide. The product can be isolated and purified by techniques well known in the art, such as extraction, evaporation, chromatography, and recrystallization.

Alternatively, for example, an acid of formula 23 is contacted with 1.2 to 1.7 equivalents of a suitable base, such as N-methylmorpholine, in a suitable solvent, such as tetrahydrofuran. As above, if the salt of an appropriate amine is used, about an additional molar amount of a suitable base is added. The reaction mixture is cooled to a temperature of between $-50°$ C. and $0°$ C. with $-25°$ C. to $-20°$ C. being preferred, before the addition of 1.2 to 1.7 equivalents of isobutyl chloroformate. The reaction is allowed to stir for 30 minutes to 3 hours to allow for the formation of the mixed anhydride. While maintaining the temperature at between $-50°$ C. and $0°$ C. an appropriate amine is added. The reaction may, after the addition of amine is complete, be warmed to room temperature. Generally, the reaction requires from 2 to 48 hours. The product can be isolated and purified by techniques well known in the art, such as extraction, evaporation, chromatography, and recrystallization.

In Reaction Scheme C, step 4, a protected 4-aryl-4-carboxamido-piperidine of formula 24 is deprotected to give a piperidine of formula 3. The removal of amine protecting groups is well known and appreciated in the art and is described in *Protecting Groups in Organic Synthesis* by T. Greene, Wiley-Interscience (1981).

In Reaction Scheme C, optional step 5, a 4-aryl-4-cyanopiperidine of formula 22 is hydrolyzed and deprotected to give a piperidine of formula 3 in which $R_7$ and $R_8$ are hydrogen. In Reaction Scheme C, optional step 5, the use of 4-aryl-4-cyanopiperidine of formula 22 in which $Pg_1$ is benzyl is preferred.

For example, an appropriate a 4-aryl-4-cyanopiperidine of formula 22 is contacted with basic hydrogen peroxide to give a 4-aryl-4-carboxylic acid amide--piperidine N-oxide. The use of basic hydrogen peroxide for the hydrolysis of nitrites to carboxamides is well know and appreciated in the art. *Reagents for Organic Synthesis*, Fieser and Fieser, John Wiley and Sons, Inc. (1967). Alkali metal hydroxides, such as sodium hydroxide or potassium hydroxide are suitable bases for this reaction. The reaction is carried out in a suitable solvent, such as water, ethanol, methanol, water/ethanol mixtures, or water/methanol mixtures. The reaction is carried out at temperatures of from $0°$ C. to the refluxing temperature of the suitable solvent. Generally, the reaction requires from about 4 hours to 4 days. The product can be isolated and purified by techniques well known in the art, such as extraction, evaporation, trituration, chromatography, and recrystallization. The 4-aryl-4-carboxylic acid amide-piperidine N-oxide is reduced and deprotected to give a piperidine of formula 3 in which $R_7$ and $R_8$ are hydrogen. It is understood that the amine deprotection and amine oxide reduction may be carried out at the same time or may be carried out sequentially. The reduction of amine oxides is also well known in the art. After reduction of the N-oxide the amine protecting group, $Pg_1$, is removed. The removal of amine protecting groups, such as benzyl and substituted benzyl is well known and appreciated in the art and is described in *Protecting Groups in Organic Synthesis* by T. Greene, Wiley-Interscience (1981). The product can be isolated and purified by techniques well known in the art, such as filtration, extraction, evaporation, trituration, chromatography, and recrystallization.

The following examples and preparations present typical syntheses of the compounds of formula (1). These examples are understood to be illustrative only and are not intended to limit the scope of the invention in any way.

PREPARATION 1

2-Methoxy-5-(1H-tetrazol-1-yl)benzoyl chloride

Combine 2-hydroxy-5-nitrobenzoic acid (21.5 g, 117 mmol), potassium carbonate (162.3 g, 1.174 mol), and methyl iodide (136.8 g, 96.4 mmol) in acetone (500 mL). Heat to reflux. After 18 hours, cool the reaction mixture to ambient temperature and add methyl iodide (136.8 g, 96.4 mmol). Again, heat to reflux. After 56 hours, cool the reaction mixture to ambient temperature and filter, rinse with acetone, and evaporate the filtrate invacuo to give a residue. Recrystallize the residue from ethanol to give a second residue. Combine the second residue and chloroform (about 100 mL), filter and evaporate the filtrate invacuo to give methyl 2-methoxy-5-nitrobenzoate. $R_f=0.38$ (silica gel, ethyl acetate/hexane 1/1).

Combine methyl 2-methoxy-5-nitrobenzoate (13.3 g, 63 mmol) and methanol. Add 5% palladium-on-carbon (0.66 g). Hydrogenate on a pressure apparatus at 50 psi. After 17 hours, filter through celite to remove the catalyst and evaporate the filtrate invacuo to give a residue. Combine the residue and dichloromethane and extract with water. Dry the organic layer over $Na_2SO_4$, filter, and evaporate invacuo to give methyl 2-methoxy-5-aminobenzoate. $R_f=0.18$ (silica gel, ethyl acetate/methanol 1/1). Elemental Analysis calculated for $C_9H_{11}NO_3$: C, 59.66; H, 6.12; N, 7.73. Found: C, 59.44; H, 6.04; N, 7.62.

Combine methyl 2-methoxy-5-amincbenzoate (3.94 g, 21.7 mmol) and triethyl orthoformate (12.8 g, 86.7 mmol) in glacial acetic acid (20 mL). After 20 hours, concentrate the reaction mixture invacuo to remove ethanol. Add glacial acetic acid (20 mL) and sodium azide (5.64 g, 86.7 mmol). Heat to $70°$ C. After 1 hour, add glacial acetic acid (10 mL) and continue to heat to $70°$ C. After an additional hour, cool the reaction mixture to ambient temperature, dilute with water (500 mL). Collect the solid by filtration, rinse with water, and dry to give methyl 2-methoxy-5-(1H-tetrazol-1-yl)benzoate.

Combine methyl 2-methoxy-5-(1H-tetrazol-1-yl)benzoate (2.86 g, 12.2 mmol) and a 1 M aqueous solution of sodium hydroxide (13.43 mL, 13.43 mmol) in methanol/water (100 mL, 5:1 vol./vol.). Heat to reflux. After 4 hours, concentrate in vacuo to remove most of the methanol, add water (50 mL), and adjust the pH to about 4 using a 1M aqueous hydrochloric acid solution. Evaporate in vacuo to give a solid, slurry the solid with water, filter, and dry to give 2-methoxy-5-(1H-tetrazol-1-yl)benzoic acid.

Alternately, combine methyl 2-methoxy-5-(1H-tetrazol-1-yl)benzoate (13.3 g, 56.8 mmol) and methanol (150 mL). Add 1M aqueous solution of sodium hydroxide (62.5 mL, 62.5 mmol). Heat to reflux. After 30 minutes, add methanol (50 mL) and water (50 mL) and continue the heat at reflux. After 1 hour, concentrate invacuo to remove most of the solvent. Adjust the pH to about 1 to 2 using a 1M aqueous hydrochloric acid solution to give a solid. Collect the solid by filtration, rinse with water, and dry to give 2-methoxy-5-(1H-tetrazol-1-yl)benzoic acid.

Combine 2-methoxy-5-(1H-tetrazol-1-yl)benzoic acid (1.2 g, 5.5 mmol) and dichloromethane (40 mL). Add dropwise oxalyl chloride (0.72 mL, 8.25 mmol) followed by dimethylformamide (3 drops). After 4 hours, evaporate in vacuo and dry to give the title compound.

PREPARATION 2

4-Phenylpiperidine-4-carboxylic acid morpholine amide hydrochloric acid salt

Combine 4-cyano-4-phenylpiperidine hydrochloric acid salt (20.0 g, 89.8 mmol) and an aqueous solution of potassium hydroxide (1.2 L, 3M, 3.6 mol). Heat to reflux. After 15 hours, cool the reaction mixture in an ice-bath and adjust the pH to about 2 using a 12M aqueous hydrochloric acid solution to give a solid. Collect the solid by filtration and dry to give 4-phenylpiperidine-4-carboxylic acid hydrochloric acid salt: $R_f$=0.2 (silica gel, 85/10/5, chloroform/methanol/acetic acid). Elemental Analysis calculated for $C_{12}H_{16}NO_2 \cdot HCl$ C, 59.63; H, 6.67; N, 5.79. Found: C, 58.19; H, 6.52; N, 5.72.

Combine 4-phenylpiperidine-4-carboxylic acid hydrochloric acid salt (2.42 g, 10 mmol), N,N-diisopropylethylamine (1.91 mL, 11 mmol), and di-t-butyl dicarbonate (2.4 g, 11 mmol) in dimethylformamide (100 mL). After 30 hours, dilute the reaction mixture with ethyl acetate and extract with 1M aqueous hydrochloric acid solution. Dry the organic layer over $MgSO_4$, filter, and concentrate invacuo to give, after drying, 1-t-butoxycarbonyl-4-phenylpiperidine-4-carboxylic acid: $R_f$=0.48 (silica gel, 6% methanol in dichloromiethane, stains brown with ninhydrin). Elemental Analysis calculated for $C_{17}H_{24}NO_4$: C, 66.86; H, 7.59; N, 4.59. Found: C, 66.56; H, 7.72; N, 4.52.

Combine 12-t-butoxycarbonyl-4-phenylpiperidine-4-carboxylic acid (1.22 g, 4 mmol) and tetrahydrofuran (40 mL). Cool to −10° C. Add triethylamine (0.61 mL, 4.4 mmol) followed by isobutylchloroformate (0.57 mL, 4.4 mmol). After the addition is complete, ambient temperature. After 15 hours, filter the reaction mixture, rinse the solids with tetrahydrofuran, and cool the filtrate to −10° C. Add morpholine (0.87 g, 10 mmol). After 0.5 hours, warm to ambient temperature. After 15 hours, filter the reactmix mixture, dilute the filtrate with ethyl acetate, and extract three times with a saturated aqueous solution of sodium bicarbonate. Dry the organic layer over $MgSO_4$, filter, and concentrate inuacuo to give 1-t-butoxycarbonyl-4-phenylpiperidine-4-carboxylic acid morpholine amide.

Alternately, combine 1-t-butoxyc.arbonyl-4-phenylpiperidine-4-carboxylic acid (1.22 g, 4 mmol), N,N-diisopropylethylamine (0.77 mL, 4.4 mmol), 1-ethyl-3-(3-dimethylaminopropyl)carbodiimide hydrochloric acid salt (0.84 g, 4.4 mmol), and 1-hydroxybenztriazole hydrate (0.59 g, 4.4 mmol) in dichloromethane (40 mL). After 12 hours, add morpholine (0.87 g, 10 mmol). After 15 hours, filter the reaction mixture, dilute the filtrate with ethyl acetate, and extract three times with a saturated aqueous solution of sodium bicarbonate. Dry the organic layer over $MgSO_4$, filter, and concentrate invacuo to give 1-t-butoxycarbonyl-4-phenyl-piperidine-4-carboxylic acid morpholine amide.

Combine 1-t-butoxycarbonyl-4-phenylpiperidine-4-carboxylic acid morpholine amide (3 mmol) and dichloromethane (20 mL). Add a solution of hydrochloric acid in dioxane (10 mL, 4M, 40 mmol). After 18 hours, evaporate invacuo to give the title compound.

Also prepared by the method of Preparation 2 are:

a) 4-phenylpiperidine-4-carboxylic acid piperidine amide hydrochloric acid salt using piperidine;

b) 4-phenylpiperidine-4-carboxylic acid pyrrolidine amide hydrochloric acid salt using pyrrolidline;

c) 4-phenylpiperidine-4-carboxylic acid piperazine amide hydrochloric acid salt using piperazine;

d) 4-phenylpiperidine-4-carboxylic acid 4-methylpiperazine amide hydrochloric acid salt using 4-methylpiperazine.

EXAMPLE 1

1-(2-Methoxy-5-(1H-tetrazol-1-yl)benzoyl)-3-(2-(4-phenyl-4-(morpholin-4-ylcarboxamido)piperidin-1-yl)ethyl)-3-(3,4-dimethoxyphenyl)pyrrolidine

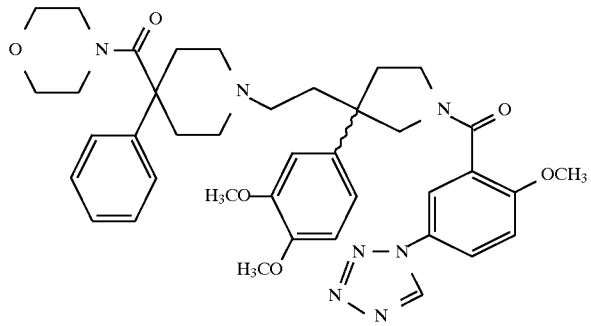

1.1 Synthesis of 3-cyano-3-(3,4-dimethoxyphenyl) pentanedioic diethyl ester

Combine 3,4-dimethoxyphenylacetonitrile (20 g, 113 mmol) and anhydrous tetrahydrofuran (100 mL). Cool in a dry-ice/acetone bath. Add dropwise a solution of sodium bis(trimethylsilyl)amide (226 mL, 1M in tetrahydrofuran, 226 mmol). When the addition is complete warm the reaction mixture to 10° C. and allow to stir for 15 minutes. Cool in a dry-ice/acetone bath, add dropwise ethyl bromoacetate (37.7 g, 226 mmol). When the addition of ethyl bromoacetate is complete, warm the reaction mixture to ambient temperature. After 18 hours, partition the reaction mixture between diethyl ether and water. Extract the organic layer with water and saturated aqueous solution of ammonium chloride. Separate the organic layer, dry over $MgSO_4$, filter, and concentrate invacuo to obtain a residue. Chromatograph the residue on silica gel eluting with 33% ethyl acetate/hexane. Remove residual solvent invacuo at 82° C. to give the title compound: $R_f$=0.37 (silica gel, 33% ethyl acetate/hexane). Elemental Analysis calculated for $C_{18}H_{23}NO_6$: C 61.88; H 6.64; N 4.01; Found: C 61.79; H 6.62; N 3.91.

2 Synthesis of (3-(3,4-dimethoxyphenyl)-5-oxopyrrolidin-3-yl)acetic acid ethyl ester Combine 3-cyano-3-(3,4-dimethoxyphenyl)pentanedioic diethyl ester (1.3 g, 3.24 mmol) and cobalt(II)chloride hexahydrate (1.54 g, 6.48 mmol) in methanol (50 mL). While maintaining the temperature at or below 20° C. with an ice-bath, add portionwise sodium borohydride (2.17 g, 57 mmol). After the addition is complete, allow the reaction mixture to stand at ambient temperature for 18 hours. Evaporate the reaction mixture invacuo to obtain a residue. Partition the residue between dichloromethane and 1M hydrochloric acid solution. Extract the aqueous layer several times with dichloromethane, combine the organic layers, dry over $Na_2SO_4$, filter, and concentrate invacuo to obtain a residue. Chromatograph the residue on silica gel eluting with 20/1 ethyl acetate/methanol. Remove residual solvent inuacuo at 82° C. to give the title compound: $R_f$=0.74 (silica gel, 5/1 ethyl acetate/methanol); mp; 116°–118° C. Elemental Analysis calculated for $C_{16}H_{21}NO_5$: C 62.53; H 6.89; N 4.56; Found: C 62.52; H 6.85; N 4.50.

1.3 Synthesis of 3-(3,4-dimethoxypheriyl)-3-(2-hydroxyethyl)pyrrolidine

Combine lithium aluminum hydride (0.99 g, 26.0 mmol) and anhydrous tetrahydrofuran (20 mL). Slowly, add (3-(3,4-dimethoxyphenyl)-5-oxopyrrolidin-3-yl)acetic acid ethyl ester (2.0 g, 6.5 mmol) as a solution in anhydrous tetrahydrofuran (40 mL). After the addition is complete. heat to reflux. After 18 hours, cool in an ice-bath. Add water (1 mL) dropwise at such a rate that the temperature of the reaction mixture does not rise above 20° C. Cool to 10° C., add 15% sodium hydroxide solution (1.0 mL). Add water (3 mL). After 15 minutes, filter the reaction mixture and concentrate the filtrate invacuo to give the title compound: $R_f$=0.68 (silica gel, 5/1 ethyl acetate/methanol).

Prepare an analytical sample as follows: Combine 3-(3,4-dimethoxyphenyl)-3-(2-hydroxyethyl)pyrrolidine (0.51 g, 2.02 mmol) and oxalic acid (0.18 g, 2.00 mmol) in tetrahydrofuran (70 mL). After 18 hours, filter and dry. Triturate with diethyl ether (100 mL), filter and dry in vacuo at 81° C. to give the title compound as its oxalate salt: mp; 140°–142° C. Elemental Analysis calculated for $C_{14}H_{21}NO_3 \cdot C_2H_2O_4$: C 56.30; H 6.79; N 4.10; Found: C 56.15; H 6.76; N 4.13.

1.4.1 Synthesis of 1-(2-methoxy-5-(1H-tetrazol-1-yl)benzoyl)-3-(3,4-dimethoxyphenyl)-3 -(2-hydroxyethyl)pyrrolidine Combine 3-(3,4-dimethoxyphenyl)-3-(2-hydroxyethyl) pyrrolidine (2.27 g, 9.03 mmol) and N-methylmorpholine (2.48 mL, 22.6 mmol) in anhydrous dichloromethane (100 mL). Cool the reaction mixture to −5° C. with an salt-ice bath. Slowly, add 2-methoxy-5-(1H-tetrazol-1-yl)benzoyl chloride (9.5 mmol) as a solution in dichloromethane (30 mL). Warm to ambient temperature. After 18 hours, extract the reaction mixture with a saturated solution of potassium carbonate. Dry the organic layer over $Na_2SO_4$, filter, and concentrate invacuo to obtain the title compound.

1.4.2 Synthesis of 1-(2-methoxy-5-(1H-tetrazol-1-yl)benzoyl)-3-(3,4-dimethoxyphenyl)-3 -(2-hydroxyethyl)pyrrolidine Combine 3-(3,4-dimethoxyphenyl)--3-(2-hydroxyethyl) pyrrolidine (5.34 g, 21.2 mmol) and sodium carbonate (1.24 g, 11.7 mmol) in ethyl acetate/water (4/1) (120 mL). Cool the reaction mixture to −5° C. with an salt-ice bath. Slowly, add 2-methoxy-5-(1H-tetrazol-1-yl)benzoyl chloride (22.3 mmol) as a solution in ethyl acetate (60 mL) at a rate such that the temperature of the reaction mixture does not rise above 0° C. Maintain the reaction temperature at about 0° C. After 18 hours, separate the organic layer. Extract the organic layer twice with 1M aqueous hydrochloric acid solution, saturated solution of sodium bicarbonate, water and a saturated solution of sodium chloride. Dry the organic layer over $Na_2SO_4$, filter, and concentrate in vacuo to obtain a residue. Combine the aqueous layers and neutralize with a saturated solution of sodium bicarbonate. Extract the neutralized aqueous layers with dichloromethane. Dry the organic layer over $Na_2SO_4$, filter, and concentrate in vacuo to obtain the title compound.

1.5 Synthesis of 1-(2-methoxy-5-(1H-tetrazol-1-yl) benzoyl)-3-(3,4-dimethoxyphenyl)-3-(2-methanesulfonyloxyethyl)pyrrolidine Combine 1-(2-methoxy-5-(1H-tetrazol-1-yl)benzoyl)-3-(3,4-dimethoxyphenyl)-3-(2-hydroxyethyl)pyrrolidine (0.43 g, 0.97 mmol), triethylamine (3.3 mL, 2.4 mmol), and anhydrous dichloromethane (30 mL). Cool the reaction mixture to −5° C. with an salt-ice bath. Slowly, add methanesulfonyl chloride (0.082 mL, 1.06 mmol) at such a rate that the temperature of the reaction mixture does not rise above 2° C. Warm to ambient temperature. After 18 hours, quench the reaction by the addition of ice. Separate the organic layer and extract 3 times with 1M hydrochloric acid solution and 2 times with a saturated solution of sodium bicarbonate. Dry the organic layer over $Na_2SO_4$, filter, and concentrate invacuo to obtain the title compound.

1.6 Synthesis of 1-(2-methoxy-5-(1H-tetrazol-1-yl) benzoyl)-3-(2-(4-phenyl-4-(morpholin-4-ylcarboxamido)piperidin-1-yl)ethyl)-3-(3,4-dimethoxyphenyl)pyrrolidine Combine 1-(2-methoxy-5-(1H-tetrazol-1-yl)benzoyl)-3-(3,4-dimethoxyphenyl)-3-(2-methanesulfonyloxyethyl) pyrrolidine (1.64 mmol), 4-phenylpiperidine-4-carboxylic acid morpholine amide hydrochloric acid salt (1.97 mmol), sodium iodide (0.25 g, 1.64 mmol), and N,N-diisopropylethylamine (0.84 g, 6.6 mmol) in acetonitrile (12 mL). Heat to reflux. After 10 hours, cool and dilute the reaction mixture ethyl acetate. Extract three times with a saturated aqueous ammonium chloride solution, twice with a saturated aqueous sodium bicarbonate solution, and then brine. Dry the organic layer over $Na_2SO_4$, filter, and evaporate invacuo to give the title compound.

PREPARATION 3

4-Phenylpiperidine-4-carboxylic acid amide hydrochloric acid salt

Combine thionyl chloride (25.4 g, 130 mmol) and chloroform (20 mL). Add over about 1 hour, a solution of N,N-bis(2-hydroxyethyl)benzylamine (25.4 g, 130 mmol) in chloroform (20 mL). After the addition is complete, heat to reflux. After 1 hour, cool the reaction mixture to ambient temperature and add diethyl ether to form a solid. Collect the solid by filtration, rinse with diethyl ether, and dry to give N,N-bis(2-chloroethyl)benzylamine hydrochloric acid salt.

Combine phenylacetonitrile (40 mmol), and aqueous sodium hydroxide solution (60 mL, 50% by weight). Add N,N-bis(2-chloroethyl)benzylamine hydrochloric acid salt (11.28 g, 42 mmol) and hexadecyltriethyl phosphonium bromide (1.02 g, 2 mmol). Heat to 100° C and stir vigorously. After 1 hour, cool the reaction mixture to ambient temperature. Add water and acidify the diluted reaction mixture with an aqueous 6M hydrochloric acid solution. Extract the acidified reaction mixture with diethyl ether. Adjust the pH of the aqueous layer to about 12 using solid potassium hydroxide and extract with ethyl acetate. Separate the ethyl acetate layer, dry over MgSO$_4$, filter, and evaporate invacuo to give a residue. Combine the residue and a solution of hydrochloric acid in methanol. Evaporate in vacuo to give 1-benzyl-4-phenyl-4-cyanopiperidine hydrochloric acid salt.

Alternately, combine 4-phenyl-4-cyano-piperidine hydrochloric acid salt (10 g, 44.9 mmol), benzyl bromide (5.4 mL, 45.4 mmol), and potassium carbonate (25.2g, 182.3 mmol) in tetrahydrofuran/water (80 mL/20 mL). After 18 hours, partition the reaction mixture between water and dichloromethane. Separate The organic layer and extract with water, dry over MgSO$_4$, filter and evaporate invacuo to give a residue. Recrystallize the residue from hexane to give 1-benzyl-4-phenyl-4-cyanopiperidine as a solid: mp; 73°–74° C.

Combine 1-benzyl-4-phenyl-4-cyanopiperidine (535 g, 1940 mmol), aqueous sodium hydroxide (85 mL, 50% by weight), and ethanol (5 L). Heat to 50° C. Remove the heating and add a solution of hydrogen peroxide (856 mL, 30% by weight in water) at such a rate that the temperature of the reaction mixture does not rise above 50° C. After the addition of hydrogen peroxide is complete, maintain the temperature of reaction mixture at 50° C. After 20 hours, dilute the reaction mixture with water (3 L) and concentrate invacuo at 35° C. to remove the ethanol. Cool the reaction mixture to ambient temperature to give a solid. Collect the solid by filtration, rinse with water, and air dried to give 1-benzyl-4-phenylpiperidine-4-carboxylic acid amide N-oxide.

Combine 1-benzyl-4-phenylpiperidine-4-carboxylic acid amide N-oxide (529 g, 1700 mmol), 10% palladium-on-carbon (25 g), and acetic acid (5 L) in an autoclave. Flush the autoclave with nitrogen and then charge with 255 psi of hydrogen. Stir while recharging the autoclave with hydrogen as required to maintain the pressure above 100 psi. When hydrogen consumption ceases, flush the autoclave with nitrogen remove the catalyst by filtration. Evaporate the filtrate invacuo to give a residue. Dissolve the residue in ethyl acetate (5 L), acidify by the addition of 12M aqueous hydrochloric acid solution (150 mL), and heat to reflux for 15 minutes. Cool the mixture to 5° C. to give solid. Collect the solid by filtration, rinse with ethyl acetate, and air dry to give the title compound.

EXAMPLE 2

(R)-1-(2-Methoxy-5-(1H-tetrazol-1-yl)benzoyl)-3-(2-(4-henyl-4-carboxamidopiperidin-1-yl)ethyl)-3-(3,4-ichlorophenyl)pyrrolidine

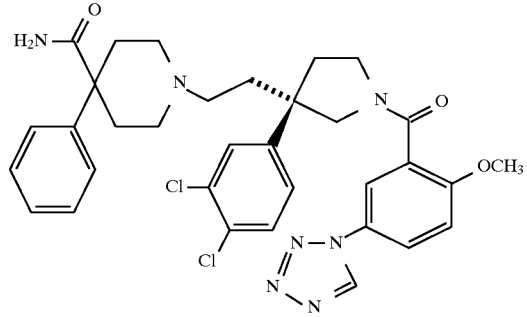

2.1.1 Synthesis of 3-cyano-3-(3,4-dichlorophenyl)pentanedioic acid diethyl ester Prepare by the method of Example 1.1 using 3,4-dichlorophenylacetonitrile (30.0 g, 0.161 mol). Purify by recrystallization from diethyl ether to give the title compound: R$_f$=0.28 (silica gel, 20% ethyl acetate/hexane), mp; 68°–69° C. Elemental Analysis calculated for C$_{16}$H$_{17}$Cl$_2$NO$_4$: C 53.65; H 4.78; N 3.91; Found: C 53.69; H 4.79; N 3.93.

2.1.2 Synthesis of 3-cyano-3-(3,4-dichlorophenyl)pentanedioic acid diethyl ester Cool a solution of sodium bis(trimethylsilyl)amide (480 lb, 1M in THF) to about −10° C. and stir. Add a solution of 3,4-dichlorophenylacetonitrile in methyl t-butyl ether (34.5% by weight, 125 lb of solution) at such a rate that the temperature of the reaction mixture does not rise above about 10° C. Combine ethyl bromoacetate (94 lb) and methyl t-butyl ether (about 125 lb) and cool to about −18° C. and then add the solution prepared above over 60–90 minutes. After the reaction is complete, as determined by chromatography, add water (18 gal). Add a 12M aqueous hydrochloric acid solution until the pH is about 4. If the pH falls below 3, use 20% aqueous sodium hydroxide solution to raise the pH to about 4. Separate the layers and extract the organic layer with brine. Evaporate in vacuo at about 40° C. to give a residue. Combine the residue and isopropanol (about 45 lb) and evaporate invacuo at about 40° C. to give a residue. Add isopropanol (190 lb), warm to about 35° C., and then cool to about −10° C. to give a solid. Collect the solid by filtration, rinse with cold isopropanol, and centrifuge to give the title compound as a wet cake containing isopropanol.

2.2.1 Synthesis of (3-(3,4-dichlorophenyl)-5-oxopyrrolidin-3-yl)acetic acid ethyl ester Prepare by the method of Example L.2 using 3-cyano-3-(3,4-dichlorophenyl)pentanedioic acid diethyl ester (10 g, 28 mmol). Purify by chromatography on silica gel eluting sequentially with 3% methanol/dichloromethane and then 6% methanol/dichloromethane to give the title compound.

2.2.2 Synthesis of (3-(3,4-dichlorophenyl)-5-oxopyrrolidin-3-yl)acetic acid ethyl ester Combine 3-cyano-3-(3,4-dichlorophenyl)pentanedioic acid diethyl ester (32 g, 89 mmol) and ethanol (150 mL) in a Parr bottle. Add Raney nickel (100 g) and an aqueous concentrated ammonia solution (40 mL),. Hydrogenate at 50 psi for 24 h. Filter through a celite pad and rinse the solids with ethanol. Evaporate the filtrate invacuo to obtain a residue. Chromatograph the residue on silica gel eluting with 6% methanol/dichloromethane to give the title compound: $R_f$=0.34 (silica gel, 6% methanol/dichloromethane); mp; 87°–90° C. Elemental Analysis calculated for $C_{14}H_{15}Cl_2NO_3$: C 53.18; H 4.78; N 4.43; Found: C 53.:34; H 4.71; N 4.51.

2.2.3 Synthesis of (3-(3,4-dichlorophenyl)-5-oxopyrrolidin-3-yl)acetic acid ethyl ester Combine Raney nickel (24 lb) and an aqueous concentrated ammonia solution (19 lb). Add a solution of 3-cyano-3-(3,4-dichlorophenyl)pentanedioic acid diethyl ester (15 lb) and ethanol (117 lb) in a pressure reactor. Hydrogenate at 200 psi and 35° C. After 20 hours, cool, vent the vessel, purge with nitrogen, and filter. Rinse the solids with ethanol. Evaporate the filtrate invacuo to give a residue. Crystallize the residue by dissolving in ethyl acetate and triturate the solution with heptane to give a solid. Collect the solid to give the title compound. Elemental Analysis calculated for $C_{14}H_{15}Cl_2NO_3$: C 53.18; H 4.78; N 4.43; Found: C 53.113; H 4.72; N 4.46.

2.2.4 Synthesis of (3-(3,4-dichlorphienyl)-5-oxopyrrolidin-3-yl)acetic acid ethyl ester Combine 3-cyano-3-(3,4-dichlorophenyl)pentanedioic acid diethyl ester (6.7 kg, wet cake containing isopropanol, about 3% L.O.D.) and 3 C ethanol (52 kg) in a pressure reactor. Add Raney nickel in water (17.5 kg, about 11 kg of active catalyst) and an aqueous concentrated ammonia solution (8.7 kg). Hydrogenate at 200 psi and 35° C. When the reaction is complete, cool, vent the reactor, and purge with nitrogen. Filter through a filter bag, rinse with ethanol, and then filter through a 0.2 micron cartridge filter, and rinse the solids with ethanol. Evaporate the filtrate invacuo to give the title compound.

2.2.5 Synthesis of (3-(3,4-dichlorophenyl)-5-oxopyrrolidin-3-yl)acetic acid ethyl ester Combine Raney nickel (twice washed with water and twice washed with ethanol, 3.6 k g), 3-cyanae-3-(3,4-dichlorophenyl)pentanedioic acid dieterhyl ester (1260 g, 3.51 mol), ethanol (9 L), and an aqueous concentrated ammonia solution (1.6 L) in a 5 gallon autoclave. Hydrogenate at 55 psi. After 20 hours, vent the vessel, purge with nitrogen, and filter. Rinse the solids with ethanol (about 1 L). Evaporate the filtrate invacuo to give a residue. Combine the residue and ethyl acetate (10 L) and extract twice with water (1 L) and then with brine. Dry the organic layer over $MgSO_4$, filter, and concentrate in vacuo to give a residue. Crystallize the residue from ethyl acetate (about 1.8 L) and heptane (about 7.2 L) to give a solid. Collect the solid to give the title compound: mp; 98°–99° C.

2.3.1 Synthesis of (3-(3,4-dichlorophenyl)-3-(2-hydroxyethyl)pyrrolidine

Cool a solution of lithium aluminum hydride (450 mL, 1M in tetrahydrofuran, 450 mmol) to –10° C. in a ice/acetone bath. Add dropwise, a solution of sulfuric acid (12 mL, 99.999%, 225.3 mmol) in tetrahydrofuran (35 mL). (Use caution when adding the sulfuric acid to the tetrahydrofuran and also when adding the sulfuric acid/tetrahydrofuran solution to the lithium aluminum hydride solution). After the addition is complete, stir for 1 hour. Warm to ambient temperature and stir for 2 hours. Add dropwise, a solution of (3-(3,4-dichlorophenyl)-5-oxopyrrolidin-3-yl)acetic acid ethyl ester (23.2 g, 73.4 mmol) in tetrahydrofuran (70 mL). Heat to 45°–50° C. for 36 hours. Cool in an ice bath. Add dropwise, a solution of tetrahydrofuran/water (1/1, 70 mL). Filter and rinse the filter cake with Tetrahydrofuran and dichloromethane, retain the filtrate. Combine the filter cake with tetrahydrofuran/water/15% sodium hydroxide solution (1 L/70 mL/20 mL) and vigorously stir for 2 hours. Filter and combine the filtrate with the filtrate obtained above. Concentrate the combined filtrates invacuo to obtain a residue. Dissolve the residue in dichloromethane and dry over $MgSO_4$, filter, and concentrate invacuo to obtain a residue. Recrystallize the residue from diethyl ether to give the title compound: $R_f$=0.27 (silica gel, 9/1/0.2 dichloromethane/methanol/ammonium hydroxide); mp; 91°–94° C.

Elemental Analysis calculated for $C_{12}H_{15}Cl_2NO$: C 55.40; H 5.81; N 5.38; Found: C 55.64; H 5.88; N 5.20.

2.3.2 Resolution of (S)-3-(3,4-dichlorophenyl)-3-(2-hydroxyethyl)pyrrolidine (R,R)-di-p-anisoyltartaric acid salt and (R)-3-(3,4-dichlorophenyl)-3-(2-hydroxyethyl)pyrrolidine (R,R)-di-p-anisoyltartaric acid salt Combine 3-(3,4-dichlorophenyl)-3-(2-hydroxyethyl)pyrrolidine (1.0 g, 38.5 mmol) and butanone. Add a solution of (R,R)-di-p-anisoyltartaric acid (1.6 g, 38.0 mmol) in butanone (80 mL). Heat to reflux. After 15 minutes, cool to ambient temperature and then cool further in an salt-ice bath. Filter the solid that forms and rinse with butanone. Recrystallize the solid from water/methanol to give (S)-(–)-3-(3, 4-dichlorophenyl)-3-(2-hydroxyethyl)pyrrolidine (R,R)-di-p-anisoyltartaric acid salt: mp; 201°–204° C. (dec). $[\alpha]^{20}_D$= –18.9°(c=0.60, dimethylsulfoxide). X-ray diffraction analysis of a single crystal confirms the (S)-configuration. Analysis on HPLC, on an analytical sample of the free amine obtained by extraction, using a CHIRALPAK AD 25 cm×0.46 cm column eluting with pentane/methanol/triethylamine (80/10/0.1) with a flow rate of 1.0 mL/minute indicates an enantiomeric excess of 96%, (96% ee), retention time of the (S)-isomer 11.2 minutes, retention time of the (R)-isomer 14.5 minutes.

2.3.3 Resolution of (S)-3-(3,4-dichlorophenyl)-3-(2-hydroxyethyl)pyrrolidine (R,R)-di-p-anisoyltartaric acid salt and (R)-3-(3,4-dichlorophenyl)-:3-(2-hydroxyethyl)pyrrolidine hydrochloric acid salt Combine (R,R)-di-p-anisoyltartaric acid (0.8 g, 19 mmol) and aqueous 12M hydrochloric acid solution (0.16 mL, 19 mmol) in water/methanol (10 mL)/(10 mL). Heat to reflux. Add dropwise, a solution of 3-(3,4-dichlorophenyl)-3-(2-hydroxyethyl)pyrrolidine (1.0 g, 38.5 mmol) in methanol (10 mL). After 15 minutes, slowly cool to ambient temperature. Filter the solid that forms and rinse with water to give (S)-3-(3,4-dichlorophenyl)-3-(2-hydroxyethyl)pyrrolidine (R,R)-di-p-anisoyltartaric acid: mp; 201°–204° C. (dec). Analysis by HPILC, as described in Example 2.3.2 indicates an enantiomeric excess of 97%, (97% ee).

2.3.4 Synthesis and resolution of (S)-3-(3,4-dichlorophenyl)-3-(2-hydroxyethyl)pyrrolidine (R, R)-di-p-anisoyltartaric acid salt Combine (3-(3,4-dichlorophenyl)-5-oxopyrrolidin-3-yl)-acetic acid ethyl ester (40 lb) and tetrahydrofuran (260 lb).

Purge the vessel with nitrogen. Add a solution of borane dimethylsulfide complex (38 lb, 2M solution in tetrahydrofuran). Heat to reflux. After 60 hours, distill until the internal temperature rises to about 70° C. and then slowly quench the reaction with methanol (650 lb). Add water (650 lb). Add methanesulfonic acid (16 lb). Heat to reflux and remove the distillate to remove most of the residual tetrahydrofuran. Combine methanol (about 18 gal) and (R,R)-di-p-anisoyltartaric acid (32 lb). Heat to reflux and transfer to the vessel containing the above residue. Add seed crystals and slowly cool to 10° C. to give a solid. Collect the solid and combine methanol (145 gal) and water (145 gal). Heat to reflux. After 1 hour, slowly cool to 10° C. to give a solid. Collect the solid to give, after drying, the title compound.

2.4.1 Synthesis of (S)-1-(2-methoxy-5-(1H-tetrazol-1-yl)benzoyl)-3-(3,4-dichlorophenyl)-3-(2-hydroxyethyl)pyrrolidine Combine (S)-3-(3,4-dichlorophenyl)-3-(2-hydroxyethyl)pyrrolidine (R,R)-di-p-anisoyltartaric acid salt (0.14 g, 0.21 mmol) ethyl acetate (15 mL), acetonitrile (6 mL), water (6 mL), and sodium bicarbonate (0.09 g, 1.03 mmol). Cool to 0° C. in an salt-ice bath. Add 2-methoxy-5-(1H-tetrazol-1-yl)benzoyl chloride (0.21 mmol). After 30 minutes, warm to ambient temperature. After 30 minutes at ambient temperature, partition the reaction mixture between ethyl acetate and brine. Extract the organic layer with 1M hydrochloric acid solution, then saturated aqueous sodium bicarbonate solution. Dry the organic layer over MgSO$_4$, filter, and evaporate in vacuo to give the title compound.

2.4.2 Synthesis of (S)-1-(2-methoxy-5-(1H-tetrazol-1-yl)benzoyl)-3-(3,4-dichlorophenyl)-3-(2-hydroxyethyl)pyrrolidine Combine (S)-3-(3,4-dichlorophenyl.)-3-(2-hydroxyethyl)pyrrolidine (R,R)-di-p-anisoyltartaric acid salt (6.0 g, 8.84 mmol) acetone (40 mL), water (40 mL), sodium hydroxide (0.335 g, 8.87 mmol)i, and sodium bicarbonate (3.73 g, 8.87 mmol). Cool to about 0° C. Add a solution of 2-methoxy-5-(1H-tetrazol-1-yl)benzoyl chloride (9.7 mmol) in acetone (12 mL) over about 15 minutes. After 3 hours, partition the reaction mixture between ethyl acetate and brine. Extract the organic layer with 1M sodium hydroxide solution, saturated sodium bicarbonate solution, 1M hydrochloric acid solution, then brine. Dry the organic layer over MgSO$_4$, filter,, and evaporate in vacuo to give the title compound.

2.4.3 Synthesis of (S)-1-(2-methoxy-5-(1H-tetrazol-1-yl)benzoyl)-(3-(3,4-dichlorophenyl)-3-(2-hydroxyethyl)pyrrolidine Combine (S)-3-(3,4-dichlorophenyl)-3-(2-hydroxyethyl)pyrrolidine (R,R)-di-p-anisoyltartaric acid salt (1.20 g, 1.77 mmol) and sodium bicarbonate (0.75 g, 8.9 mmol) in acetone/water (5 mL/5 mL). Cool in an ice bath. Add 2-methoxy-5-(1H-tetrazol-1-yl)benzoyl chloride (0.37 g, 1.6 mmol) in acetone (20 mL). After 30 minutes, warm to ambient temperature. After 5 hours, filter the reaction mixture and extract the filtrate with ethyl acetate. Extract the organic layer with a saturated aqueous sodium bicarbonate solution and then brine. Dry the organic layer over MgSO$_4$, filter, and evaporate invacuo to give residue. Chromatograph the residue on silica gel eluting sequentially with ethyl acetate, 3% methanol/ dichloromethane, and then 6% methanol/dichloromethane to give the title compound: R$_f$=0.38 (silica gel, 6% methanol/dichloromethane).

2.5.1 Synthesis of (S)-1-(2-methoxy-5-(1H-tetrazol-1-yl)benzoyl)-3-(3,4-dichlorophenyl)-3-(2-methanesulfonyloxyethyl)pyrrolidine Prepare by the method of Example 1.5 using (S)-1-(2-methoxy-5-(1H-tetrazol-1-yl)benzoyl)-3-(3,4-dichlorophenyl)-3-(2-hydroxyethyl)pyrrolidine and methanesulfonyl chloride to give the title compound.

2.5.2 Synthesis of (S)-1-(2-methoxy-5-(1H-tetrazol-1-yl)benzoyl)-3-(3,4-dichlorophenyl)-3-(2-methanesulfonyloxyethyl)pyrrolidine Combine (S)-1-(2-methoxy-5-(1H-tetrazol-1-yl)benzoyl)-3-(3,4-dichlorophenyl)-3-(2-hydroxyethyl)pyrrolidine (600 mg, 1.3 mmol) and N,N-diisopropylethylamine (0.5 mL, 2.87 mmol) in dichloromethane (13 mL). Cool in a ice-bath. Add dropwise, methanesulfonyl chloride (0.12 mL, 1.55 mmol). After 15 minutes add more methanesulfonyl chloride (0.03 mL, 0.39 mmol). After 30 minutes, extract with 5% sodium bicarbonate solution and water. Dry the organic layer over MgSO$_4$, filter, and concentrate invacuo to give the title compound: R$_f$=0.15 (silica gel, ethyl acetate).

2.5.3 Synthesis of (S)-1-(2-methoxy-5-(1H-tetrazol-1-yl)benzoyl)-3-(3,4-dichlorophenyl)-3-(2-methanesulfonyloxyethyl)pyrrolidine Combine (S)-1-(2-methoxy-5-(1H-tetrazol-1-yl)benzoyl)-3-(3,4-dichlorophenyl)-3-(2-hydroxyethyl)pyrrolidine (200 mg, 0.44 mmol) and N-methylmorpholine (0.97 mmol) in toluene (10 mL). Add dropwise, methanesulfonyl chloride (0.066 g, 0.57 mmol). After 12 hours, dilute with toluene (20 mL) and extract with 1M hydrochloric acid solution and 5% sodium bicarbonate solution. Dry the organic layer over MgSO$_4$, filter, and concentrate invacuo to give the title compound.

2.6 Synthesis of 1-(2-methoxy-5-(1H-tetrazol-1-yl)benzoyl)-3-(2-(4-phenyl-4-carboxamidopiperidin-1-yl)ethyl)-3-(3,4-dichlorophenyl)pyrrolidine Prepare by the method of Example 1.6 using 1-(2-methoxy-5-(1H-tetrazol-1-yl)benzoyl)-3-(3,4-dichlorophenyl)-3-(2-methanesulfonyloxyethyl)pyrrolidine and 4-phenylpiperidine-4-carboxylic acid amide hydrochloric acid salt to give the title compound.

EXAMPLE 3

1-(2-Methoxy-5-(1H-tetrazol-1-yl)benzoyl)-3-(2-(4-phenyl-4-carboxamidopiperidin-1-yl)ethyl)-3-phenylpyrrolidine

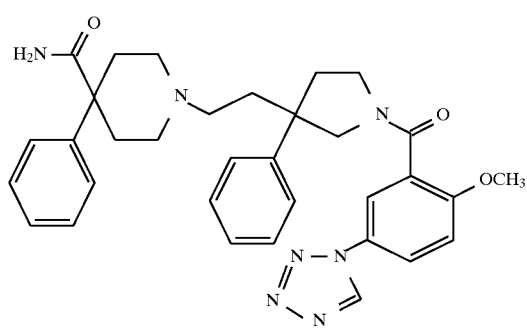

3.1.1 Synthesis of 3-cyano-3-phenylpentanedioic acid diethyl ester

Prepare by the method of Example 1.1 using phenylacetonitrile (5.85 g, 50.0 mmol). Purify by chromatography on silica gel eluting with 20% ethyl acetate in hexane to obtain the title compound: $R_f$=0.23 (silica gel, 20% ethyl acetate in hexane).

3.1.2 Synthesis of 3-cyano-3-phenyl)entanedioic acid diethyl ester

Combine phenylacetonitrile (5.85 g, 50.0 mmol) and tetrahydrofuran (140 mL). Cool to about 5° C. Add dropwise, a solution of sodium bis(trimethylsilyl)amide (800 mL, 1M in tetrahydrofuran, 800 mmol). When the addition is complete, warm the reaction mixture to ambient temperature and allow to stir for 1 hour. Transfer the above solution via cannula into a cooled (−8° C.) solution of ethyl bromoacetate (84.5 mL, 762 mmol) in tetrahydrofuran (500 mL) at such a rate that the temperature of the reaction mixture does not rise above about 20° C. Allow to stir at ambient temperature. After 18 hours, dilute with diethyl ether (1.5 L) and extract with saturated aqueous solution of ammonium chloride, then water, and then saturated aqueous solution of sodium chloride. Dry the organic layer over $MgSO_4$, filter, and concentrate invacuo to obtain a residue. Distill the residue by bulb-to-bulb distillation to give the title compound: bp; 140°–150° C. at 0.2 mm Hg.

3.1.3 Synthesis of 3-cyano-3-phenylpentanedioic acid diethyl ester

Combine phenylacetonitrile (175.5 g, 1.5 mol) and tetrahydrofuran (1.95 L). Cool to about 0° C. Add dropwise over about 15 minutes, a solution of sodium bis (trimethylsilyl)amide (3.2 L, 1M in tetrahydrofuran, 3.2 mol). When the addition is complete, warm the reaction mixture to ambient temperature and allow to stir for 1 hour. Transfer the above solution over about 45 minutes into a cooled (about −20° C.) solution of ethyl bromoacetate (510 g, 3.05 mol) in tetrahydrofuran (1.95 L). Warm to ambient temperature and allow to stir. After 18 hours, dilute with diethyl ether (3 L) and water (1.5 L). Extract twice with saturated aqueous solution of ammonium chloride (2.25 L) and then brine. Dry the organic layer over $MgSO_4$, filter, and concentrate invacuo to obtain a residue. Distill the residue by bulb-to-bulb distillation to give the title compound: bp; 180°–190° C. at 30 mm of Hg. Elemental Analysis calculated for $C_{16}H_{19}NO_4$: C, 66.43; H, 6.62; N, 4.84. Found: C, 66.34; H, 6.57; N, 4.82.

3.2.1 Synthesis of (3-phenyl-5-oxopyrrolidin-3-yl) acetic acid ethyl ester

Prepared by the method of Example 2.2.2 using 3-cyano-3-phenylpentanedioic acid diethyl ester to give the title compound: $R_f$=0.60 (silica gel, 6% methanol/dichloromethane).

3.2.2 Synthesis of (3-phenyl-5-oxopyrrolidin-3-yl) acetic acid ethyl ester

Combine 3-cyano-3-phenylpentanedioic acid diethyl ester (93 g, 321 mmol) and ethanol (400 mL) in a 2 gallon pressure reactor. Add Raney nickel (280 g). Heat to 50° C. and charge with 200 psi of hydrogen. After 15 minutes, vent the reactor and add aqueous concentrated ammonia solution (120 mL). Charge the reactor with 200 psi of hydrogen. After 7 hours, vent the reactor and allow to stand for 18 hours. Filter through a celite pad and rinse the solids with ethanol. Evaporate the filtrate in vacuo to obtain a residue. Combine the residue and 1/5 diethyl ether/hexane (500 mL) and cool to −20° C. After 18 hours, decant and add 1/5 diethyl ether/hexane (500 mL) and cool to −20° C. to give a solid. Collect the solid by filtration and triturate with 1/5 diethyl ether/hexane (500 mL). Filter and dissolve in diethyl ether (300 mL) and add hexane (700 mL) to give a solid. Collect the solid by filtration and dry to give the title compound. Elemental Analysis calculated for $C_{14}H_{17}NO_3$: C 68.00; H 6.93; N 5.66; Found: C 67.63; H 6.99; N 5.81.

3.2.3 Synthesis of (3-phenyl-5-oxopyrrolidin-3-yl) acetic acid ethyl ester

Combine 3-cyano-3-phenylpentanedioic acid diethyl ester (396.6 g, 1.37 mol) and ethanol (4 L), and concentrated aqueous ammonia (530 mL), in a two gallon autoclave. Add Raney nickel (410 g). Heat to 24° C. and charge with 205 psi of hydrogen. After 26 hours, vent the reactor and purge with nitrogen. Filter the reaction mixture through a celite pad and rinse the solids with ethanol (1.5 L). Evaporate the filtrate in vacuo to give the title compound.

3.2.4 Synthesis of (3-phenyl-5-oxopyrrolidin-3-yl) acetic acid ethyl ester

Combine 3-cyano-3-phenylpentanedioic acid diethyl ester (243 g, 0.84 mol) and ethanol (2.5 L), concentrated aqueous ammonia (325 mL), and Raney nickel (250 g, prewashed three times with water) in a two gallon autoclave. Charge with 200 psi of hydrogen. Heat to 50° C. After 24 hours, vent the reactor and purge with nitrogen. Filter the reaction mixture through a celite pad and rinse the solids with ethanol (1 L). Evaporate the filtrate in vacuo to give the title compound.

3.3.1 Synthesis of 3-phenyl-3-(2-hydroxyethyl) pyrrolidine

Prepare by the method of Example 1.3 using (3-phenyl-5-oxopyrrolidin-3-yl)acetic acid ethyl ester (8.7 g, 35 mmol) to give, after recrystallization from dichloromethane/diethyl ether, the title compound: mp; 115.0°–117.0° C; $R_f$=0.03 (silica gel, 6% methanol/dichloromethane). Elemental Analysis calculated for $C_{12}H_{17}NO$: C 75.36; H 8.96; N 7.32; Found: C 75.78; H 8.96; N 7.45.

3.3.2 Synthesis of 3-phenyl-3-(2-hydroxyethyl) pyrrolidine

Combine (3-phenyl-5-oxopyrrolidin-3-yl)acetic acid ethyl ester (301 g, 1.25 mol) and tetrahydrofuran (3.5 L). Cool to about 5° C. Slowly, add portionwise over about 45 minutes a solution of lithium aluminum hydride in tetrahydrofuran (3.9 L, 1M, 3.9 mol). After the addition is complete heat to 60° C. After 18 hours, cool in an ice-bath. Add water/tetrahydrofuran 1/1 (1.95 L) dropwise at such a rate that the temperature of the reaction mixture does not rise above 20° C. Dilute the reaction mixtur tetrahydrofura tetrahydrofuran (2.25 L) and stir. After 1.5 hours, filter the reaction mixture. Suspend the solids in diethyl ether (3 L) and filter. Combine the filtrates and concentrate the in vacuo to give a residue. Combine the residue and dichloromethane (4 L) and extract three times with water (1 L). Dry the organic layer over $MgSO_4$, filter, and concentrate in vacuo to obtain a solid. Triturate the solid with diethyl ether (0.3 L), collect by filtration, rinse with diethyl ether, and dry to give the title compound: $R_f$=0.12 (silica gel dichloromethane/methanol/concentrated aqueous ammonia, 9/1/0.1).

3.3.3 Synthesis of 3-phenyl-3-(2-hydroxyethyl) pyrrolidine

Combine (3-phenyl-5-oxopyrrolidin-3-yl)acetic acid ethyl ester (171 g, 0.69 mol) and tetrahydrofuran (2 L). Cool to about 5° C. Slowly, add over about 15 minutes a solution of lithium aluminum hydride in tetrahydrofuran (2.24 L, 1M, 2.24 mol). After the addition is complete heat to about 60° C. After 18 hours, cool in an ice-bath. Slowly quench by adding a saturated aqueous solution of sodium potassium tartrate (208 mL). After the quench is complete, add $Na_2SO_4$ (100 g) and celite (150 g) and stir. After 3 hours, dilute the reaction mixture with tetrahydrofuran (2 L) and filter. Suspend the solids in diethyl ether (2 L) and filter. Combine the filtrates and concentrate the in vacuo to give the title compound: mp; 106°–110° C. $R_f$=0.12 (silica gel dichloromethane/methanol/ concentrated aqueous ammonia, 9/1/0.1).

3.3.4 Resolution of (−)-3-phenyl-3-(2-hydroxyethyl) pyrrolidine (R,R)-di-p-anisoyltartaric acid salt Combine (R,R)-di-p-anisoyltartaric acid (1.10 g, 2.62 mmol) in water/methanol (13.6 mL/13.6 mL). Add 12M hydrochloric acid solution (0.217 mL, 2.63 mmol). Add a hot solution of 3-phenyl-3-(2-hydroxyethyl)pyrrolidine (1.0 g, 5.23 mmol) in methanol (13.6 mL). Heat to reflux. After 30 minutes, slowly cool to ambient temperature to give a solid. Collect the solid by filtration and recrystallize the solid twice from methanol/water, once from methanol/2-butanone, and once from ethanol to give (−)-3-phenyl-3-(2-hydroxyethyl)pyrrolidine (R,R)-di-p-anisoyltartaric acid. After conversion of a analytical sample to the 3,4,5-trimethoxybenzamide using sodium carbonate and 3,4,5-trimethoxybenzoyl chloride in acetone/water, analysis on HPLC using a CHIRALPAK AD (10μm ×4.6 cm×250 cm) column eluting with pentane/ethanol/methanol/triethylamine (80/15/5/0.1) with a flow rate of 1.5 mL/minute indicates an enantiomeric excess of 98%, (98% ee), retention time 22.30 minutes for the 3,4,5-trimethoxybenzamide of the isomer prepared from the (−)-isomer of the (R,R)-di-p-anisoyltartaric acid salt.

3.3.5 Resolution of (+)-3-phenyl-3-(2-hydroxyethyl) pyrrolidine (R,R)-di-p-anisoyltartaric acid salt and (−)-3-phenyl-3-(2-hydroxyethyl)pyrrolidine (R,R)-di-p-anisoyltartaric acid salt Add a hot solution of 3-phenyl-3-(2-hydroxyethyl)pyrrolidine (5.0 g, 20.2 mmol) in ethanol (100 mL) to a refluxing solution of (R,R)-di-p-anisoyltartaric acid (16.46 g, 20.2 mmol), containing a small amount of acetone) in ethanol (200 mL). After the addition is complete, slowly cool to ambient temperature to give a solid. Collect the solid by filtration and recrystallize the solid three times from ethanol to give (−)-3-phenyl-3-(2-hydroxyethyl)pyrrolidine (R,R)-di-p-anisoyltartaric acid salt: mp; 1716.0°–179.0° C. Elemental Analysis calculated for $C_{12}H_{17}NO \cdot C_{20}H_{18}O_{10}$: C 63.05; H 5.79; N 2.30; Found: C 62.72; H 5.80; N 2.33. After conversion of a sample to the 3,4,5-trimethoxybenzamide and analysis on HPLC by the method of Example 3.3.4 indicates an enantiomeric excess of 99.9%, (99.9% ee), retention time 22.30 minutes for the 3,4,5-trimethoxybenzamide prepared from the (−)-isomer of the (R,R)-di-p-anisoyltartaric acid salt.

Upon standing, the mother liquors from above give a solid. Collect the solid by filtration and recrystallize twice from ethanol to give (+)-3-phenyl-3-(2-hydroxyethyl)pyrrolidine (R,R)-di-p-anisoyltartaric acid salt: mp; 175.0°–176.0° C. Elemental Analysis calculated for $C_{12}H_{17}NO \cdot C_{20}H_{18}O_{10} \cdot 0.8\ C_3H_6O$: C 62.98; H 6.11; N 2.13; Found: C 62.86; H 5.94; N 2.33. After conversion of a sample to the 3,4,5-trimethoxybenzamide and analysis on HPLC by the method of Example 3.3.4 indicates an enantiomeric excess of 99.9%, (99.9% ee), retention time 10.26 minutes for the 3,4,5-trimethoxybenzamide prepared from the (+)-isomer of the (R,R)-di-p-anisoyltartaric acid salt.

3.3.6 Resolution of (+)-3-phenyl-3-(2-hydroxyethyl) pyrrolidine (R,R)-di-p-anisoyltartaric acid salt and (−)-3-phenyl-3-(2-hydroxyethyl)pyrrolidine (R,R)-di-p-anisoyltartaric acid salt Combine 3-phenyl-3-(2-hydroxyethyl)pyrrolidine (99.2 g, 659 mmol) and ethanol (2.5 L). Heat to reflux. Add a refluxing solution of (R,R)-di-p-anisoyltartaric acid (212 g, 507 mmol) in ethanol (5.07 L). After the addition is complete, slowly cool to ambient temperature with stirring to give an oil. Dissolve the oil in ethanol at reflux (595 mL) and add a refluxing solution of (R,R)-di-p-anisoyltartaric acid (49.2 g) in ethanol (1.1 L). Cool to ambient temperature with stirring to give a solid. Collect the solid by filtration and recrystallize from ethanol (3.2 L) to give a second solid. Collect the second solid by filtration and recrystallize from ethanol (2.6 L), seed with (−)-3-phenyl-3-(2-hydroxyethyl)pyrrolidine (R,R)-di-p-anisoyltartaric acid salt to give (−)-3-phenyl-3-(2-hydroxyethyl)pyrrolidine (R,R)-di-p-anisoyltartaric acid salt (121 g).

3.3.7 Resolution of (+)-3-phenyl-3-(2-hydroxyethyl) pyrrolidine (R,R)-di-p-anisoyltartaric acid salt and (−)-3-phenyl-3-(2-hydroxyethyl)pyrrolidine (R,R)-di-p-anisoyltartaric acid salt Combine 3-phenyl-3-(2-hydroxyethyl)pyrrolidine (101 g, 530 mmol) and ethanol (1.92 L). Heat to reflux. Add a refluxing solution of (R,R)-di-p-anisoyltartaric acid (107 g, 410 mmol) in ethanol (3.9 L). Continue to reflux. After 10 minutes, slowly cool to ambient temperature and add seed crystals. After 18 hours, collect the solid that forms by filtration, rinse with ethanol (200 mL). recrystallize twice from ethanol to give (−)-3-phenyl-3-(2-hydroxyethyl)pyrrolidine (R,R)-di-p-anisoyltartaric acid salt: mp; 179°–180° C. $[\alpha]_D^{20}$=−108.8(c=1.02, methanol).

3.3.8 Synthesis of (+)-3-phenyl-3-(2-hydroxyethyl) pyrrolidine hydrochloric acid salt Combine (−)-3-phenyl-3-(2-hydroxyethyl)pyrrolidine (R,R)-di-p-anisoyltartaric acid salt (30.9 g, 50.7 mmol) and sodium bicarbonate (11.6 g, 53.2 mmol) in tetrahydrofuran/water (200 mL, 5/1). Cool in ice bath and add di-t-butyl dicarbonate (8.52 g, 101 mmol). After 18 hours, evaporate in vacuo to remove most of the tetrahydrofuran. Dilute with ethyl acetate and extract with water, a saturated aqueous solution of ammonium chloride, a saturated aqueous solution of sodium bicarbonate, and then brine. Dry the organic layer over MgSO4, filter, and evaporate in vacuo to give a residue. Chromatograph the residue on silica gel eluting with 50% ethyl acetate/hexane to give 1-t-butoxycarbonyl-3-phenyl-3-(2-hydroxyethyl)pyrrolidine, prepared from (−)-3-phenyl-3-(2-hydroxyethyl)pyrrolidine (R,R)-di-p-anisoyltartaric acid salt: $R_f$=0.25 (silica gel, 50% ethyl acetate/hexane).

Combine 1-t-butoxycarbonyl-3-phenyl-3-(2-hydroxyethyl)pyrrolidine (13.0 g, 44.6 mmol) and a solution of hydrochloric acid in dioxane (22.3 mL, 4M, 89.2 mmol). Heat to 50° C. After 1 hour, cool and add diethyl ether to give a solid. Collect the solid by filtration to give, after drying, the title compound: mp; 161°–163° C. $[\alpha]_D^{20}$=+11.8 (c=0.563, methanol). Elemental Analysis calculated for $C_{12}H_{17}NO \cdot HCl$: C 63.29; H 7.97; N 6.15; Found: C 63.21; H 7.86; N 6.05.

3.4.1 Synthesis of 1-(2-methoxy-5-(1H-tetrazol-1-yl)benzoyl)-3-phenyl-3-(2-hydroxyethyl)pyrrolidine Combine (−)-3-phenyl-3-(2-hydroxyethyl)pyrrolidine (R,R)-di-p-anisoyltartaric acid salt (3.49 g, 6.48 mmol) and acetone (20 mL), water (6 mL), and potassium carbonate (2.70 g, 19.5 mmol). Cool to 0° C. in an ice bath. After 30 minutes, add dropwise a solution of 2-methoxy-5-(1H-tetrazol-1-yl)benzoyl chloride (7.4 mmol) in acetone (20 mL). Warm to ambient temperature. After 18 hours, partition the reaction mixture between ethyl acetate and saturated aqueous sodium bicarbonate solution. Separate the organic layer and extract with brine. Dry the organic layer over $Na_2SO_4$, filter, and evaporate in vacuo to give the title compound.

3.4.2 Synthesis of 1-(2-methoxy-5-(1H-tetrazol-1-yl)benzoyl)-3-phenyl-3-(2-hydroxyethyl)pyrrolidine Combine (−)-3-phenyl-3-(2-hydroxyethyl)pyrrolidine (R,R)-di-p-anisoyltartaric acid salt (56.0 g, 92.1 mmol), sodium carbonate (19.5 g, 184 mmol) in ethyl acetate (2 L) and water (2 L). Cool to about 0° C. in an ice bath. After 30 minutes, slowly add portionwise 2-methoxy-5-(1H-tetrazol-1-yl)benzoyl chloride (92.1 mmol). After the addition is complete, warm to ambient temperature. After 1 hour, dilute the reaction mixture ethyl acetate and extract with water, 1M aqueous hydrochloric acid solution, and then brine. Dry the organic layer over $Na_2SO_4$, filter, and evaporate in vacuo to give the title compound. $R_f$=0.48 (9/1 dichloromethane/methanol).

3.5 Synthesis of 1-(2-methoxy-5-(1H-tetrazol-1-yl)benzoyl)-3-phenyl-3-(2-methanesulfonyloxyethyl)pyrrolidine Prepare by the method of Example 2.5.2 using 1-(2-methoxy-5-(1H-tetrazol-1-yl)benzoyl)-3-phenyl-3-(2-hydroxyethyl)pyrrolidine (prepared from (−)-3-phenyl-3-(2-hydroxyethyl)pyrrolidine (R,R)-di-p-anisoyltartaric acid salt) to give the title compound.

3.6 Synthesis of 1-(2-methoxy-5-(1H-tetrazol-1-yl)benzoyl)-3-(2-(4-phenyl-4-carboxamidopiperidin-1-yl)ethyl)-3-phenylpyrrolidine Prepare by the method of Example 1.6 using 1-(2-methoxy-5-(1H-tetrazol-1-yl)benzoyl)-3-phenyl-3-(2-methanesulfonyloxyethyl)pyrrolidine (prepared from (−)-3-phenyl-3-(2-hydroxyethyl)pyrrolidine (R,R)-di-p-anisoyltartaric acid salt) and 4-phenylpiperidine-4-carboxylic acid amide hydrochloric acid salt to give the title compound.

EXAMPLE 4

(S)-1-(2-Methoxy-5-(1H-tetrazol-1-yl)benzoyl)-3-(2-(4-phenyl-4-carboxamidopiperidin-1-yl)ethyl)-3-(3,4-dichlorophenyl)pyrrolidine

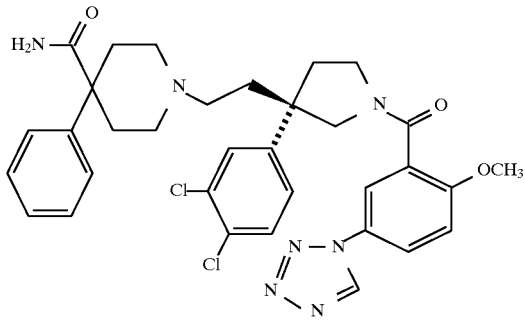

4.1 Resolution of (R)-(+)-3-(3,4-dichlorophenyl)-3-(2-hydroxyethyl)pyrrolidine (S,S)-di-p-anisoyltartaric acid salt Combine (S,S)-di-p-anisoyltartaric acid (14.77 g, 35 mmol), water (200 mL) and methanol (200 mL). Heat to reflux. Add dropwise, a solution of 3-(3,4-dichlorophenyl)-3-(2-hydroxyethyl)pyrrolidine (18.36 g, 70 mmol) in methanol (135 mL). After 1.5 hours, add water (135 mL) and slowly cool to ambient temperature to give a solid. Filter the solid that forms and rinse with water to give the title compound: mp; 201°–202° C. (dec). Analysis by HPLC, as described in Example 3.3.4 indicates an enantiomeric excess of 99.9%, (99.9% ee). $[°]^{20}_D = +17.90° (c=1.00,$ dimethylsulfoxide).

4.2 Synthesis of (R)-1-(2-methoxy-5-(1H-tetrazol-1-yl)benzoyl)-3-(3,4-dichlorophenyl)-3-(2-hydroxyethyl)pyrrolidine Prepare by the method of Example 2.4.3 using (R)-3-(3,4-dichlorophenyl)-3-(2-hydroxyethyl)pyrrolidine (R,R)-di-p-anisoyltartaric acid salt to give the title compound.

4.3 Synthesis of (R)-1-(2-methoxy-5,-(1H-tetrazol-1-yl)benzoyl)-3-(3,4-dichlorophenyl)-3-(2-methanesulfonyloxyethyl)pyrrolidine Prepare by the method of Example 2.5.2 (S)-1-(2-methoxy-5-(1H-tetrazol-1-yl)benzoyl)-3-(3,4-dichlorophenyl)-3-(2-hydroxyethyl)pyrrolidine to give the title compound.

4.4 Synthesis of (S)-1-(2-methoxy-5-(1H-tetrazol-1-yl)benzoyl)-3-(2-(4-phenyl-4-carboxamidopiperidin-1-yl)ethyl)-3-(3,4-dichlorophenyl)pyrrolidine Combine (R)-1-(2-methoxy-5-(1H-tetrazol-1-yl)benzoyl)-3-(3,4-dichlorophenyl)-3-(2-methanesulfonyloxyethyl)pyrrolidine (9 mmol), 4-phenylpiperidine-4-carboxylic acid amide hydrochloric acid salt (8 mmol), and N,N-diisopropylethylamine (4.6 g, 36 mmol) in acetonitrile (100 mL). Heat to reflux. After 19 hours, cool the reaction mixture and evaporate in vacuo to give a residue. Combine the residue and dichloromethane and extract with saturated aqueous sodium bicarbonate and then brine. Dry the organic layer over $MgSO_4$, filter, and evaporate in vacuo to give the title compound.

EXAMPLE 5

(R)-1-(2-Methoxy-5-(1H-tetrazol-1-yl)benzoyl)-3-(2-(4-phenyl-4-carboxamidopiperidin-1-yl)e thyl)-3-(3,4-dichlorophenyl)pyrrolidine

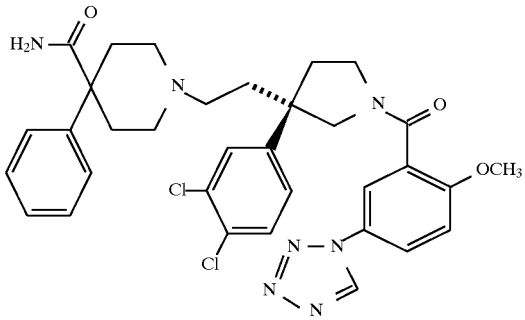

5.1 Synthesis of (S)-1-(t-butoxycarbonyl)-3-(3,4-dichlorophenyl)-3-(2-hydroxyethyl)pyrrolidine Combine (S)-3-(3,4-dichlorophenyl)-3-(2-hydroxyethyl)pyrrolidine (R,R)-di-p-anisoyltartaric acid salt (40 g, 59.0 mmol), N,N-diisopropylethylamine (20.6 mL), and dichloromethane (400 mL). Add dropwise a solution of di-t-butyl dicarbonate (14.2 g) in dichloromethane (100 mL). After 18 hours, extract the reaction mixture with saturated aqueous sodium bicarbonate! solution and then three times with water. Dry the organic layer over MgSO$_4$, filter, and evaporate in vacuo to give a residue. Chromatograph the residue on silica gel eluting sequentially with 35% ethyl acetate/hexane and then 50% ethyl acetate/hexane to the title compound: R$_f$=0.16 (silica gel, 35% ethyl acetate/hexane).

5.2 Synthesis of (S)-1-(t-butoxycarbonyl)-3-(3,4-dichlorophenyl)-3-(2-methanesulfonyloxyethyl) pyrrolidine Combine (S)-1-(t-butoxycarbonyl)-3-(3,4-dichlorophenyl)-3-(2-hydroxyethyl)pyrrolidine (17 g, 47.0 mmol), N,N-diisopropylethylamine (20 mL), and dichloromethane (300 mL). Cool the reaction mixture in an ice bath. Add dropwise methanesulfonyl chloride (4.8 mL). After 30 minutes add additional methanesulfonyl chloride (0.9 mL). After 2 hours, extract the reaction mixture with saturated aqueous sodium bicarbonate solution and then three times with water. Dry the organic layer over MgSO$_4$, filter, and evaporate in vacuo to give a residue. Chromatograph the residue on silica gel eluting sequentially with 20% ethyl acetate/hexane, 35% ethyl acetate/hexane, 50% ethyl acetate/hexane and then ethyl acetate to the title compound: R$_f$=0.24 (silica gel, 35% ethyl acetate/hexane).

5.3 Synthesis of (S)-1-(t-butoxycarbonyl)-3-(2-(4-phenyl-4-carboxamidopiperidin-1-yl)ethyl)-3-(3,4-dichlorophenyl)pyrrolidine Combine (S)-1-(t-butoxycarbonyl)-3-(3,4-dichlorophenyl)-3-(2-methanesulfonyloxyethyl)pyrrolidine (17.9 g, 40.9 mmol), 4-phenylpiperidine-4-carboxylic acid amide hydrochloric acid salt (11 g, 45.7 mmol), potassium carbonate (18 g, 130 mmol) and tetrahydrofuran/water (120 mL/40 mL). Heat to reflux. After 90 hours cool the reaction mixture to ambient temperature and separate the layers. Extract the aqueous layer with dichloromethane. Combine the organic layers, dry over MgSO$_4$, filter, and evaporate in vacuo to give a residue. Chromatograph the residue on silica gel eluting sequentially with 20% ethyl acetate/hexane, 3% methanol/dichloromethane and then 6% methanol/dichloromethane to the title compound: R$_f$=0.40 (silica gel, 6% methanol/dichloromethane).

5.4.1 Synthesis of (S)-3-(2-(4-phenyl-4-carboxamidopiperidin-1-yl)ethyl)-3-(3,4-dichlorophenyl)pyrrolidine hydrochloric acid salt Combine (S)-1-(t-butoxycarbonyl)-3-(2-(4-phenyl-4-carboxamidopiperidin-1-yl)ethyl)-3-(3,4-dichlorophenyl)pyrrolidine (1.15 g) and dichloromethane (25 mL). Cool in an ice bath. With stirring, add hydrochloric acid (gas, about 3.6 g). After 1 hour, evaporate in vacuo to give a residue. Add dichloromethane, evaporate in vacuo, and dry to give the title compound.

5.4.2 Synthesis of (S)-3-(2-(4-phenyl-4-carboxamidopiperidin-1-yl)ethyl)-3-(3,4-dichlorophenyl)pyrrolidine hydrochloric acid salt Combine (S)-1-(t-butoxycarbonyl)-3-(2-(4-phenyl-4-carboxamidopiperidin-1-yl)ethyl)-3-(3,4-dichlorophenyl)pyrrolidine (15.0 g, 27.5 mmol) and dichloromethane (200 mL). Cool in an ice bath. Add a solution of hydrochloric acid in dioxane (30 mL, 4M, 120 mmol). After 3 hours, add methanol (100 mL) and heat to about 45° C. After 12 hours, evaporate in vacuo to give the title compound.

5.5 Synthesis of (R)-1-(2-methoxy-5-(1H-tetrazol-1-yl)benzoyl)-3-(2-(4-phenyl-4-carboxamidopiperidin-1-yl)ethyl)-3-(3,4-dichlorophenyl)pyrrolidine Combine (S)-3-(2-(4-phenyl-4-carboxamidopiperidin-1-yl)ethyl)-3-(3,4-dichlorophenyl)pyrrolidine hydrochloric acid salt (1.03 g, 1.99 mmol), N,N-diisopropylethylamine (1.1 mL, 6.3 mmol) in dichloromethane (50 mL). Add 1-hydroxybenzotriazole hydrate (0.3 g, 2.22 mmol), 1-ethyl-3-(3-dimethylaminopropyl)carbodiimide hydrochloric acid salt (0.43 g, 2.22 mmol), and 2-methoxy-5-(1H-tetrazol-1-yl)benzoic acid (0.52 g, 2.35 mmol), After 18 hours, dilute the reaction mixture with dichloromethane and extract twice with water. Dry the organic layer over MgSO$_4$, filter, and evaporate in vacuo to give a residue. Chromatograph the residue on silica gel eluting sequentially with dichloromethane, 3% methanol/dichloromethane, 5% methanol/dichloromethane, and then 10% methanol/dichloromethane to give the title compound: R$_f$=0.17 (silica gel, 6% methanol/dichloromethane).

5.6 Synthesis of (R)-1-(2-methoxy-5-(1H-tetrazol-1-yl)benzoyl)-3-(2-(4-phenyl-4-carboxainidopiperidin-1-yl)ethyl)-3-(3,4-dichlorophenyl)pyrrolidine hydrochloric acid salt Combine (R)-1-(2-methoxy-5-(1H-tetrazol-1-yl)benzoyl)-3-(2-(4-phenyl-4-carboxamidopiperidin-1-yl)ethyl)-3-(3,4-dichlorophenyl)pyrrolidine (0.77 g, 1.19 mmol) and dichloromethane (20 mL). Cool in an ice bath. Add a solution of hydrochloric acid in dioxane (0.72 mL, 4M, 2.88 mmol) to give a solid. After 3 hours, collect the solid, repeatedly combine with ethanol and evaporate in vacuo to give the title compound.

PREPARATION 4

2-Methoxy-5-(4H-triazol-4-yl)benzoic acid

According to the method of *J. Chem. Soc.* (C), 1664 (1967), combine methyl 2-methoxy-5-aminobenzoate (2.0 g, 11 mmol), N,N-dimethylformamideazine (1.56 g, 11 mmol), p-toluenesulfonic acid (190 mg) in toluene (25 mL). Fit the reaction vessel with a gas inlet such that the head space of the vessel is swept with argon and scrub the effluent through dilute aqueous hydrochloric acid solution. Heat to reflux. After 20 hours, concentrate the reaction mixture in vacuo to give a residue. Partition the residue between dichloromethane and a saturated aqueous sodium bicarbonate solution. Extract the aqueous layer twice with dichloromethane. Combine the organic layers, dry over $MgSO_4$, filter, and evaporate in vacuo to give a residue. Chromatograph the residue on silica gel eluting sequentially with 70% ethyl acetate/dichloromethane and then 5% methanol/dichloromethane to give a residue. Recrystallize the residue form ethyl acetate/hexane to give methyl 2-methoxy-5-(4H-triazol-4-yl)benzoate: mp; 191°–195.5° C.

Alternately, according to the method of *J. Med. Chem.*, 21, 1100 (1978), combine methyl 2-methoxy-5-aminobenzoate (1.8 g, 10 mmol), diformyl hydrazines (0.97 g, 11 mmol), and phosphorous pentoxide (1.84 g, 13 mmol). Heat to 160° C. After 1.5 hours, cool the reaction mixture and add a saturated aqueous solution of sodium bicarbonate. Extract three times with dichloromethane. Dry the combined organic layers over $MgSO_4$, filter, and evaporate in vacuo to give a residue. Chromatograph the residue on silica gel eluting sequentially with 40% ethyl acetate/dichloromethane and then 5% methanol/dichloromethane to give methyl 2-methoxy-5-(4H-triazol-4-yl)benzoate: mp; 179°–182° C.

Combine methyl 2-methoxy-5-(4H-triazol-4-yl)benzoate (56 mmol) and methanol (200 mL) and water (50 mL). Add 1M aqueous solution of sodium hydroxide (62.5 mL, 62.5 mmol). Heat to reflux. After 8 hour, concentrate in vacuo to remove most of the solvent. Adjust the pH to about 1 to 2 using a 1M aqueous hydrochloric acid solution, extract with dichloromethane. Dry the organic layer over $MgSO_4$, filter, and evaporate in vacuo to give the title compound.

EXAMPLE 6

(R)-1-(2-Methoxy-5-(4H-triazol-4-yl)benzoyl)-3-(2-(4-phenyl-4-carboxamidopiperidin-1-yl)ethyl)-3-(3,4-5 dichlorophenyl)pyrrolidine

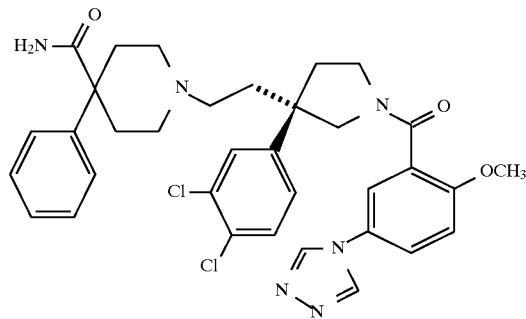

6.1 Synthesis of (R)-1-(2-methoxy-5-(4H-triazol-4-yl)benzoyl)-3-(2-(4-phenyl-4-carboxamidopiperidineethyl)-3-(3,4-dichlorophenyl) pyrrolidine Prepare by the method of Example 5.5 using (S)-3-(2-(4-phenyl-4-carboxamidopiperidin-1-yl)ethyl)-3-(3,4-dichlorophenyl)pyrrolidine hydrochloric acid salt and 2-methoxy-5-(4H-triazol-4-yl)benzoic acid to give the title compound.

6.2 Synthesis of (R)-1-(2-methoxy-5-(4H-triazol-4-yl)benzoyl)-3-(2-(4-phenyl-4-carboxamidopiperidine)ethyl)-3-(3,4-dichlorophenyl)pyrrolidine hydrochloric acid salt Prepare by the method of Example 5.6 using (R)-1-(2-methoxy-5-(4H-triazol-4-yl)benzoyl)-3-(2-(4-phenyl-4-carboxamidopiperidine)ethyl)-3-(3,4-dichlorophenyl) pyrrolidine to give the title compound.

PREPARATION 5

2-Methoxy-5-(1H-tetrazol-5-yl)benzoic acid

Combine methyl 2-methoxy-5-formylbenzoate (5.0 g, 25.9 mmol), hydroxylamine hydrochloride (8.55 g, 133 mmol), and sodium acetate (10.25 g, 125 mmol) in ethanol/water (200 mL, 1/1). Heat to 50° C. After 1 hour, pour the reaction mixture onto ice to give a solid. Collect the solid by filtration to give methyl 2-methoxy-5-formylbenzoate oxime: $R_f$=0.76 (silica gel, 9/1 dichloromethane/methanol).

Combine methyl 2-methoxy-5-formylbenzoate oxime (3.5 g, 16.7 mmol) in dichloromethane (75 mL) and cool in an ice-bath. Add dropwise thionyl chloride (2.0 mL, 27.2 mmol). After 20 minutes, dilute the reaction mixture with dichloromethane and extract with a saturated aqueous solution of sodium bicarbonate and then brine. Dry the organic layer over $MgSO_4$, filter, and concentrate in vacuo to give a residue. Chromatograph the residue on silica gel eluting with 1/1 ethyl acetate/hexane to give methyl 2-methoxy-5-cyanobenzoate.

Combine methyl 2-methoxy-5-cyanobenzoate (0.67 mmol), sodium azide (0.13 g, 2.04 mmol), and triethylammonium hydrochloride (0.14 g, 1.03 mmol) in N-methylpyrrolidinone (6 mL). Heat to 150° C. After 4 hours, cool to ambient temperature and partition the reaction mixture between water and ethyl acetate. Separate the layers and extract the aqueous layer three times with ethyl acetate. Adjust the pH of the aqueous layer to about 1 using a 1M aqueous hydrochloric acid solution. The aqueous layer is again extracted three times with ethyl acetate, and twice with dichloromethane. The aqueous layer is saturated with sodium chloride and again extracted four times with dichloromethane. Combine the organic layers, dry over $MgSO_4$, filter, and evaporate in vacuo to give methyl 2-methoxy-5-(1H-tetrazol-5-yl)benzoate.

Combine methyl 2-methoxy-5-(1H-tetrazol-5-yl) benzoate (1 mmol) and lithium hydroxide (1.1 mmol) in 1/1 tetrahydrofuran/water (5 mL). After 24 hours, dilute the reaction mixture with a 0.5M aqueous hydrochloric acid solution and dichloromethane. Separate the layers and extract the aqueous layer three times with dichloromethane. Combine the organic layers, dry over $MgSO_4$, filter, and evaporate in vacuo to give the title compound.

EXAMPLE 7

(R)-1-(2-Methoxy-5-(1H-tetrazol-5-yl)benzoyl)-3-(2-(4-phenyl-4-carboxamidopiperidin-1-yl)ethyl)-3-(3,4-dichlorophenyl)pyrrolidine

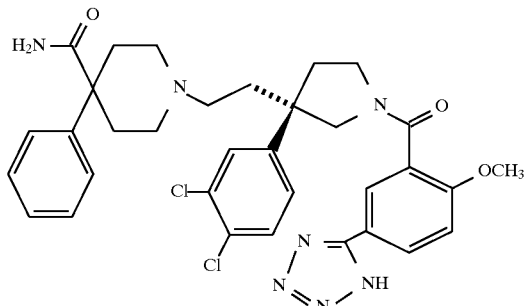

7.1 Synthesis of (R)-1-(2-methoxy-5-(1H-tetrazol-5-yl)benzoyl)-3-(2-(4-phenyl-4-carboxamidopiperidine)ethyl)-3-(3,4-dichlorophenyl)pyrrolidine Prepare by the method of Example 5.5 using (S)-3-(2-(4-phenyl-4-carboxamidopiperidin--1-yl)ethyl)-3-(3,4-dichlorophenyl)pyrrolidine hydrochloric acid salt and 2-methoxy-5-(1H-tetrazol-5-yl)benzoic acid to give the title compound.

PREPARATION 6

4-(Pyrid-3-yl)piperidine-4-carboxylic acid amide hydriodic acid salt

Combine N,N-bis-(2-chloroethyl)benzylamine hydrochloric acid salt (72.0 g, 269 mmol) and pyrid-3-ylacetonitrile (31.8 g, 269 mmol) and hexadecyltributylphosphonium bromide (6 g) in aqueous solution of sodium hydroxide (50% by weight, 400 mL). Heat on a steam bath and stir vigorously. After 1.5 hours, cool the reaction mixture to ambient temperature. Extract the reaction mixture three times with dichloromethane. Combine the organic layers and extract twice with an aqueous 10% hydrochloric acid solution. Combine the aqueous layers and make basic with an aqueous solution of sodium hydroxide (50% by weight). Extract the basified aqueous layer three times with diethyl ether. Dry the combined ether layers over MgSO$_4$ and filter to give a filtrate. Purge the filtrate with hydrogen chloride (gas) to give a solid. Collect the solid by filtration and dry in vacuo at 65° C. to give 1-benzyl-4-(pyrid-3-yl)-4-cyanopiperidine hydrochloric acid salt.

Combine 1-benzyl-4-(pyrid-3-yl)-4-cyanopiperidine hydrochloric acid salt (7.0 g, 20 mmol), aqueous sodium hydroxide (7 mL, 50% by weight), and ethanol (130 L). Heat to about 50° C. Remove the heating and add a solution of hydrogen peroxide (23 mL, 30% by weight in water) at such a rate that the temperature of the reaction mixture does not rise above 60° C. After the addition of hydrogen peroxide is complete, maintain the temperature of reaction mixture at 50° C. After 4 hours, concentrate inuacuo to give a solid. Collect the solid by filtration, rinse with water, and air dried to give 1-benzyl-4-(pyrid-3-yl N-oxide)-piperidine-4-carboxylic acid amide N-oxide; R$_f$=0.29 (silica gel, 9/1 methanol/dichloromethane).

Alternatively, combine 1-benzyl-4-(pyrid-3-yl)-4-cyanopiperidine hydrochloric acid salt (20.0 g), aqueous sodium hydroxide (20 mL, 50% by weight), and methanol (380 L). Add a solution of hydrogen peroxide (60 mL, 30% by weight in water) at such a rate that the temperature of the reaction mixture does not rise above 60° C. After the addition of hydrogen peroxide is complete, heat to about 50° C. After 2 hours, concentrate in vacuo to give a solid. Collect the solid by filtration and rinse with water to give 1-benzyl-4-(pyrid-3-yl N-oxide)-piperidine-4-carboxylic acid amide N-oxide.

Combine 1-benzyl-4-(pyrid-3-yl N-oxide)-piperidine-4-carboxylic acid amide N-oxide (3.1 g,, 10.5 mmol), 5% palladium-on-carbon (2 g), and methanol (200 mL) in a pressure apparatus. Hydrogenate at 55 psi of hydrogen. After 71 hours, remove the catalyst by filtration, rinse with methanol, and evaporate the filtrate in vacuo to give 4-(pyrid-3-yl)-piperidine-4-carboxylic acid amide.

Combine 4-(pyrid-3-yl)-piperidine-4-carboxylic acid amide (3.0 g, 14.6 mmol), methanol (:30 mL), and water (10 mL). Cool in an ice bath and add an aqueous solution of hydriodic acid (4.2 mL, 57%, 31.2 mmol). After 30 minutes, filter and evaporate the filtrate in vacuo to give a residue. Triturate the residue with methanol to give a solid. Collect the solid and dry in vacuo at 56° C. to give the title compound.

EXAMPLE 8

(R)-1-(2-Methoxy-5-(1H-tetrazol-1-yl)benzoyl)-3-(2-(4-(pyrid-3-yl)-4-carboxamidopiperidin-1-yl)ethyl)-3-(3,4-dichlorophenyl)pyrrolidine

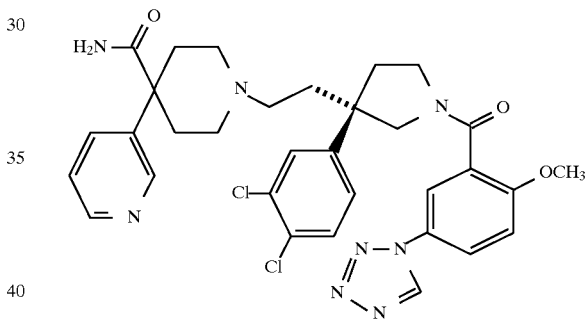

8.1.1 Synthesis of (R)-1-(2-methoxy-5-(1H-tetrazol-1-yl)benzoyl)-3-(2-(4-(pyrid-3-yl)-4-carboxamidopiperidin-1-yl)ethyl)-3-(3,4-dichlorophenyl)pyrrolidine Combine (S)-1-(2-methoxy-5-(1H-tetrazol-1-yl)benzoyl)-3-(3,4-dichlorophenyl)-3-(2-methanesulfonyloxyethyl) pyrrolidine (1.3 mmol), N,N-diisopropylethylamine (1 mL, 5.74 mmol), and 4-(pyrid-3-yl)piperidine-4-carboxylic acid amide hydriodic acid salt (0.75 g, 1.62 mmol) in acetonitrile (25 mL). Heat to reflux. After 18 hours, add methanol (15 mL) and continue to reflux. After 18 hours, cool the reaction mixture to ambient temperature, dilute with dichloromethane and extract twice with water. Dry the organic layer over MgSO$_4$, filter, and concentrate in vacuo to obtain a residue. Chromatograph the residue on silica gel eluting sequentially with ethyl acetate, 3% methanol/ethyl acetate, 6% methanol/ethyl acetate, and then 10% methanol/ethyl acetate to give the title compound.

8.1.2 Synthesis of (R)-1-(2-methoxy-5-(1H-tetrazol-1-yl)benzoyl)-3-(2-(4-(pyrid-3-yl)-4-carboxamidopiperidin-1-yl)ethyl)-3-(3,4-dichlorophenyl)pyrrolidine Combine (S)-1-(2-methoxy-5-(1H-tetrazol-1-yl)benzoyl)-3-(3,4-dichlorophenyl)-3-(2- methanesulfonyloxyethyl) pyrrolidine (1.6 mmol), potassium carbonate (1.1 g, 8.0 mmol), and 4-(pyrid-3-yl)piperidine-4-carboxylic acid amide (0.50 g, 2.44 mmol) in tetrahydrofuran/water (9 mL/3 mL). Heat to reflux. After 100 hours, cool the reaction mixture to ambient temperature and dilute with dichloromethane. Filter and extract the filtrate twice with water. Dry the organic layer over MgSO$_4$, filter, and concentrate in vacuo to obtain a residue. Chromatograph the residue on silica gel eluting sequentially with ethyl acetate, 3% methanol/ethyl acetate, 6% methanol/ethyl acetate, and then 10% methanol/ethyl acetate to give the title compound.

8.2 Synthesis of (R)-1-(2-methoxy-5-(1H-tetrazol-1-yl)benzoyl)-3-(2-(4-(pyrid-3-yl)-4-carboxamidopiperidin-1-yl)ethyl)-3-(3,4-dichlorophenyl)pyrrolidine hydrochloric acid salt Combine (R)-1-(2-methoxy-5-(1H-tetrazol-1-yl)benzoyl)-3-(2-(4-(pyrid-3-yl)-4-carboxamidopiperidin-1-yl)ethyl)-3-(3,4-dichlorophenyl)pyrrolidine (0.3 g) and dichloromethane (50 mL). Cool in an ice bath. Add hydrochloric acid (gas, about 6.0 g). After 1 hour, add methanol (about 20 mL) and evaporate in vacuo to give, after drying in vacuo at 56° C., the title compound.

EXAMPLE 9

1-(2-Methoxy-5-(1H-tetrazol-1-yl)benzoyl)-3-(2-(4-phenyl-4-carboxamidopiperidin-1-yl)ethyl)-3-(3,4-dimethylphenyl)pyrrolidine

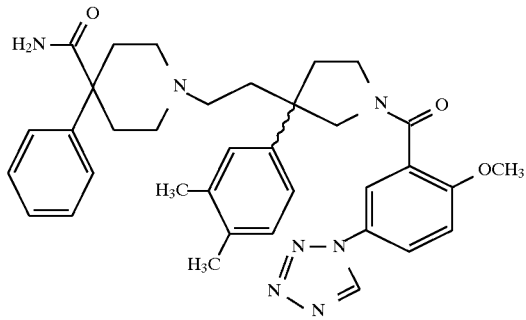

9.1.1 Synthesis of 3-cyano-3-(3,4-dimethylphenyl)pentanedioic acid diethyl ester Combine 3,4-dimethylphenylacetonitrile (50.0 mmol) and tetrahydrofuran (140 mL). Cool to about 5° C. Add dropwise a solution of sodium bis(trimethylsilyl)amide (800 mL, 1M in tetrahydrofuran, 800 mmol). When the addition is complete, warm the reaction mixture to ambient temperature and allow to stir for 1 hour. Transfer the above solution via cannula into a cooled (−8° C.) solution of ethyl bromoacetate (84.5 mL, 762 mmol) in tetrahydrofuran (500 mL) at such a rate that the temperature of the reaction mixture does not rise above 20° C. Allow to stir at ambient temperature. After 18 hours, dilute with diethyl ether (1.5 L) and extract with saturated aqueous solution of ammonium chloride, then water, and then saturated aqueous solution of sodium chloride. Dry the organic layer over MgSO$_4$, filter, and concentrate invacuo to give the title compound.

9.1.2 Synthesis of 3-cyano-3-(3,4-dimethylphenyl)pentanedioic acid diethyl ester Cool a solution of sodium bis(trimethylsilyl)amide (723 mL, 1M in tetrahydrofuran, 723 mmol) to 0° C. in an ice bath. Add a solution of 3,4-dimethylphenylacetonitrile (50.0 mmol) in tetrahydrofuran (130 mL) over about 1.5 hours. When the addition is complete, warm the reaction mixture to ambient temperature and allow to stir. After 2 hours, transfer the above solution via cannula into a cooled (−50° C.) solution of ethyl bromoacetate (126 g, 757 mmol) in tetrahydrofuran (250 mL). After the transfer is complete, allow the reaction mixture to warm to ambient temperature. After 18 hours, dilute with diethyl ether (500 mL) and extract with water, 1M hydrochloric acid solution, saturated aqueous solution of sodium bicarbonate, and then brine. Dry the organic layer over MgSO$_4$, filter, and concentrate in vacuo to give a residue. Recrystallize the residue from diethyl ether to give the title compound as a solid.

9.2.1 Synthesis of (3-(3,4-dimethylphenyl)-5-oxopyrrolidin-3-yl)acetic acid ethyl ester Prepare by the method of Example 2.2.2 using 3-cyano-3-(3,4-dimethylphenyl)pentanedioic acid diethyl ester to give the title compound.

9.2.2 Synthesis of (3-(3,4-dimethylphenyl)-5-oxopyrrolidin-3-yl)acetic acid ethyl ester Combine 3-cyano-3-(3,4-dimethylphenyl)pentanedioic acid diethyl ester (56 g, 177 mmol) and ethanol (500 mL) in a Parr bottle. Add Raney nickel (50 g) and an aqueous concentrated ammonia solution (85 mL). Hydrogenate at 50° C. and 100 psi for 48 h. Filter through a celite pad and rinse the solids with ethanol. Evaporate the filtrate in vacuo to obtain a residue. Chromatograph the residue on silica gel eluting with 6% methanol/dichloromethane to give the title compound.

9.3 Synthesis of 3-(3,4-dimethylphenyl)-3-(2-hydroxyethyl)pyrrolidine

Prepare by the method of Example 2.3.1 using (3-(3,4-dimethylphenyl)-5-oxopyrrolidin-3-yl)acetic acid ethyl ester to give, after recrystallization from dichloromethane/diethyl ether, the title compound: R$_f$=0.35 (silica gel, 85/10/5 dichloromethane/methanol/acetic acid).

9.4 Synthesis of 1-(2-methoxy-5-(1H-tetrazol-1-yl)benzoyl)-(3-(3,4-dimethylphenyl)-3-(2-hydroxyethyl)pyrrolidine Combine 3-(3,4-dimethylphenyl)-3-(2-hydroxyethyl)pyrrolidine (20 mmol) and sodium bicarbonate (8.4 g) in acetone (50 mL)/water (50 mL). Add a solution of 2-methoxy-5-(1H-tetrazol-1-yl)benzoyl chloride (20 mmol) in acetone (50 mL). After 3 hours, extract the reaction mixture three times with ethyl acetate. Dry the organic layer over MgSO$_4$, filter, and concentrate in vacuo to give the title compound.

9.5 Synthesis of 1-(2-methoxy-5-(1H-tetrazol-1-yl)benzoyl)-3-(3,4-dimethylphenyl)-3-(2-methanesulfonyloxyethyl)pyrrolidine Prepare by the method of Example 2.5.2 using 1-(2-methoxy-5-(1H-tetrazol-1-yl)benzoyl)-3-(3,4-dimethylphenyl)-3-(2-hydroxyethyl)pyrrolidine to give the title compound.

9.6 Synthesis of 1-(2-methoxy-5-(1H-tetrazol-1-yl)benzoyl)-3-(2-(4-phenyl-4-carboxamidopiperidin-1-yl)ethyl)-3-(3,4-dimethylphenyl)pyrrolidine Prepare by the method of Example 1.6 using 1-(2-methoxy-5-(1H-tetrazol-1-yl)benzoyl)-3-(3,4- dimethylphenyl)-3-(2-methanesulfonyloxyethyl)pyrrolidine and 4-phenylpiperidine-4-carboxylic acid amide hydrochloric acid salt to give the title compound.

PREPARATION 7

3-(1H-Tetrazol-1-yl)benzoic acid

Prepare ethyl 3-(1H-tetrazol-1-yl)benzoate by the method of Preparation 1 using ethyl 3-aminobenzoate to give ethyl 3-(1H-tetrazol-1-yl)benzoate: $R_f$=0.51 (silica gel, 1/1 ethyl acetate/hexane).

Combine ethyl 3-(1H-tetrazol-1-yl)benzoate (4.93 g, 22.6 mmol) and tetrahydrofuran/water (100 mL/25 mL). Add lithium hydroxide (1.9 g, 45.2 mmol) and heat to reflux. After 2 hours, cool to ambient temperature and extract the reaction mixture five times with a 1M aqueous sodium hydroxide solution. Combine the aqueous layers and extract with ethyl acetate. Acidify the aqueous layers with a 1M aqueous hydrochloric acid solution (pH about 1) to give a solid. Collect the solid by filtration to give the title compound.

EXAMPLE 10

(R)-1-(3-(1H-Tetrazol-1-yl)benzoyl)-3-(2-(4-phenyl-4-carboxamidopiperidin-1-yl)ethyl)-3-(3,4-dichlorophenyl)pyrrolidine

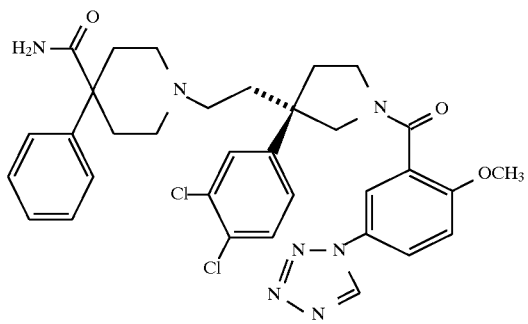

10.1 Synthesis of (R)-1-(3-(1H-tetrazol-1-yl)benzoyl)-3-(2-(4-phenyl-4-carboxamidopiperidin-1-yl)ethyl)-3-(3,4-dichlorophenyl)pyrrolidine Prepare by the method of Example 5.5 using (S)-3-(2-(4-phenyl-4-carboxamidopiperidin-1-yl)ethyl)-3-(3,4-dichlorophenyl)pyrrolidine hydrochloric acid salt and 3-(1H-tetrazol-1-yl)benzoic acid to give the title compound.

PREPARATION 8

2-Methyl-5-(1H-tetrazol-1-yl)benzoic acid

Combine 2-methyl-5-nitrobenzoic acid (4.98 g, 27.5 mmol), potassium carbonate (1.93 g, 14.0 mol), and methyl iodide (7.80 g, 55.0 mmol) in acetone (100 mL). Heat to reflux. After 4 hours, cool the reaction mixture, dilute with water, and extract five times with ethyl acetate. Combine the organic layers, extract with a saturated aqueous sodium bicarbonate solution and then brine. Dry the organic layer over $Na_2SO_4$, filter, and evaporate in vacuo to give methyl 2-methyl-5-nitrobenzoate: $R_f$=0.61 (silica gel, ethyl acetate/hexane 1/1).

Combine methyl 2-methyl-5-nitrobenzoate (5.32 g, 27.2 mmol) and methanol (100 mL). Add 5% palladium-on-carbon (0.27 g). Hydrogenate on a pressure apparatus at 50 psi. After 18 hours, filter through celite to remove the catalyst and evaporate the filtrate in vacuo to give methyl 2-methyl-5-aminobenzoic acid: $R_f$=0.34 (silica gel, ethyl acetate/hexane 1/4).

Combine methyl 2-methyl-5-aminobenzoate (4.5 g, 27.2 mmol) and triethyl orthoformate (16.2 g, 109 mmol) in glacial acetic acid (25 mL). After 12 hours, add portionwise sodium azide (7.08 g, 109 mmol). Heat to 70° C. After 2 hours, cool the reaction mixture to ambient temperature, dilute with water (250 mL). Collect the solid by filtration, rinse with water, and dry to give methyl 2-methyl-5-(1H-tetrazol-1-yl)benzoate: $R_f$=0.13 (silica gel, ethyl acetate/hexane 1/4).

Combine methyl 2-methyl-5-(1H-tetrazol-1-yl)benzoate (5.2 g, 23.9 mmol) and lithium hydroxide hydrate (2.0 g, 47.7 mmol) in tetrahydrofuran/water (50 mL/50 mL). Heat to reflux. After 2 hours, dilute with diethyl ether and separate the layers. Extract the aqueous layer three times with diethyl ether. Extract the combined diethyl ether layers three times with a 1M sodium hydroxide solution (20 mL). Combine the aqueous layers, acidify with a 1M aqueous hydrochloric acid solution (pH about 1) to give a solid. Collect the solid by filtration and recrystallize form water to give the title compound.

EXAMPLE 11

(R)-1-(2-Methyl-5-(1H-tetrazol-1-yl)benzoyl)-3-(2-(4-phenyl-4-carboxamidopiperidin-1-yl)ethyl)-3-(3,4-dichlorophenyl)pyrrolidine

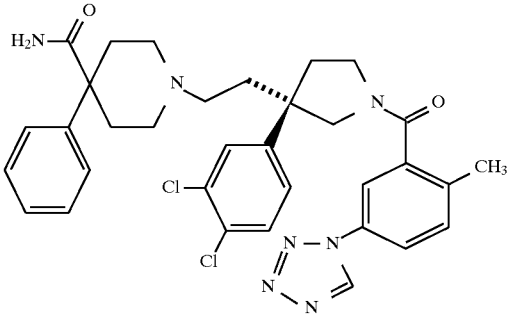

11.1 Synthesis of (R)-1-(2-methyl-5-(1H-tetrazol-1-yl)benzoyl)-3-(2-(4-phenyl-4-carboxamidopiperidin-1-yl)ethyl)-3-(3,4-dichlorophenyl)pyrrolidine Prepare by the method of Example 5.5 using (S)-3-(2-(4-phenyl-4-carboxamidopiperidin-1-yl)ethyl)-3-(3,4-dichlorophenyl)pyrrolidine hydrochloric acid salt and 2-methyl-5-(1H-tetrazol-1-yl)benzoic acid to give the title compound.

The tachykinins are a class of neuropeptides which share a common C-terminus sequence, Phe-Xaa-Gly-Leu-Met-$NH_2$. The tachykinins are widely distributed in the peripheral and central nervous systems where they bind to at least three receptors types. The $NK_1$, $NK_2$, and $NK_3$ receptors are defined by the preferred binding affinity of substance P, neurokinin A (NKA), and neurokinin B (NKB), respectively.

The use of tachykinin antagonists is indicated as therapy for a variety of tachykinin-mediated diseases and conditions including: cystitis; bronchoconstriction; hypersensitivity reactions; the treatment of pain; peripheral neuropathy; post-herpetic neuralgia; adverse immunological reactions; respiratory diseases, such as asthma, bronchitis, cough, rhinitis, and allergies and the like; opthalmic diseases, such as conjuctivitis and vernal conjuctivitis; cutaneous diseases, such as contact dermatitis, atopic dermatitis, and urticaria; inflammatory diseases, such as rheumatoid arthritis and osteoarthritis, and the like; gastrointestinal conditions, such as Crohn's disease, emesis, and ulcerative colitis; conditions due to vasodilation, such as angina and migraine; and central nervous system diseases and conditions, such as anxiety, depression, psychosis, schizophrenia, dementia.

It is understood that tachykinin-mediated diseases and conditions are those diseases and conditions in which the tachykinins are involved, either in whole or in part, in their clinical manifestation(s). Moreover, the tachykinins involvement is not necessarily causative of a particular tachykinin-mediated disease and condition. Tachykinin antagonists are useful in controlling or providing therapeutic relief of those tachykinin-mediated diseases and conditions.

The present invention provides new and useful tachykinin antagonists of formula (1), and stereoisomers and pharmaceutically acceptable salts thereof. Particularly, the present invention provides compounds of formula (1) which are $NK_1$ and $NK_2$ receptor antagonists.

In a further embodiment, the present invention provides a method of treating tachykinin-mediated diseases and conditions in a patient in need thereof comprising administering to said patient a therapeutically effective amount of a compound of formula (1). Various diseases and conditions described to be treated herein, are well known and appreciated by those skilled in the art. It is also recognized that one skilled in the art may affect the associated diseases and conditions by treating a patient presently afflicted with the diseases or conditions or by prophylactically treating a patient afflicted with the diseases or conditions with a therapeutically effective amount of the compounds of formula (1).

As used herein, the term "patient" refers to a warm blooded animal such as a mammal which is afflicted with a particular tachykinin-mediated disease or condition. It is understood that guinea pigs, dogs, cats, rats, mice, horses, cattle, sheep, and humans are examples of animals within the scope of the meaning of the term. A patient is in need of treatment for tachykinin-mediated diseases and conditions when the patient is inflicted within one or more of the diseases or conditions described herein.

The identification of those patients who are in need of treatment of a tachykinin-mediated disease or condition is well within the ability and knowledge of one skilled in the art. A clinician skilled in the art can readily identify, by the use of clinical tests, physical examination and medical/family history, those patients who are in need of such treatment.

As used herein, the term "therapeutically effective amount" of a compound of formula (1) refers to an amount which is effective in controlling tachykinin-mediated diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment of the tachykinin-mediated diseases and conditions.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of involvement or the severity of the disease; the response of the individual patient; the particular compound administered; the mode of administration; the bioavailability characteristic of the preparation administered; the dose regimen selected; the use of concomitant medication; and other relevant circumstances.

A therapeutically effective amount of a compound of formula (1) is expected to vary from about 0.1 milligram per kilogram of body weight per day (mg/kg/day) to about 100 mg/kg/day. Preferred amounts are able to be determined by one skilled in the art.

In effecting treatment of a patient afflicted with tachykinin-mediated diseases and conditions described above, a compound of formula (1) can be administered in any form or mode which makes the compound bioavailable in an effective amount, including oral, inhalation, parenteral, and topical routes. For example, compounds of formula (1) can be administered orally, by inhalation of an aerosol or dry powder, subcutaneously, intramuscularly, intravenously, intranasally, rectally, transdermally, topically, and the like. Oral or inhalation administration is generally preferred for treatment of respiratory diseases and conditions, e.g. asthma, bronchitis, and cough. One skilled in the art of preparing formulations can readily select the proper form and mode of administration depending upon the particular characteristics of the compound selected, the disease or condition to be treated, the stage of the disease or condition, and other relevant circumstances. (Remington's Pharmaceutical Sciences, 18th Edition, Mack Publishing Co. (1990)).

The compounds of the present invention can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, such as acid addition salts or base addition salts, for purposes of stability, convenience of crystallization, increased solubility and the like.

In another embodiment, the present invention provides pharmaceutical compositions comprising a therapeutically effective amount of a compound of formula (1) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds of formula (I) may be incorporated with excipieznts and used in the form of tablets, troches, capsules, elixirs, suspensions, syrups, wafers, chewing gums and the like. These preparations should contain at least: 4% of the compound of Formula (I), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders such as microcrystalline cellulose, gum tragacanth or gelatin; excipients such as starch or lactose, disinte- grating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1% and about 50% of the weight thereof. The amount of the active ingredient present in such compositions is such that a suitable dosage will be obtained. Preferred compositions and preparations are able to be determined by one skilled in the art.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

The compounds of the present invention may also be administered by inhalation, such as by aerosol or dry powder. Delivery may be by a liquefied or compressed gas or by a suitable pump system which dispenses the compounds of the present invention or a formulation thereof. Formulations for administration by inhalation of compounds of formula (1) may be delivered in single phase, bi-phasic, or tri-phasic systems. A variety of systems are available for the administration by aerosol of the compounds of formula (1). Dry powder formulations are prepared by either pelletizing or milling the compound of formula (1) to a suitable particle size or by admixing the pelletized or milled compound of formula (1) with a suitable carrier material, such as lactose and the like. Delivery by inhalation includes the necessary container, activators, valves, subcontainers, and the like. Preferred aerosol and dry powder formulations for administration by inhalation can be determined by one skilled in the art.

The compounds of the present invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula (1) or its pharmaceutical salt from about 0.1 to about 10% w/v (weight per unit volume).

The tachykinin receptor antagonists of the present invention can be evalutated by the procedures that follow.

EXAMPLE A

Antagonism of iodinated tachykinin binding to $NK_1$ and $NK_2$ receptors by putative antagonists One skilled in the art can determine the $NK_1$ receptor and $NK_2$ receptor affinity in vitro as follows. The $NK_1$ receptor affinity of tachykinin antagonists is evaluated in guinea pig lungs (Keystone Biologicals, Cleveland, Ohio) and affinity for the $NK_2$ receptor is evaluated in HSKR-1 cells (which are mouse 3T3 fibroblasts expressing the human jejunal $NK_2$ receptor). Tissues or cells are homogenized with a Polytron in 15 volumes of 50 mM Tris-HCl buffer (pH 7.4, 4° C.) and centrifuged. The pellet is resuspended in Tris-HCl buffer and is centrifuged; the pellet is washed twice by resuspension. The final pellet is resuspended at a concentration of 40 mg/ml for tissues and 20 mg/ml for cells in incubation buffer and remains at room temperature for at least 15 min prior to use. Receptor binding is initiated by addition of 250 ul membrane preparation in duplicate to 0.1 nM of the following radioligands: $^{125}$I-Bolton Hunter Lys-3 labeled substance P and $^{125}$iodohistidyl-l-neurokinin A; in a final volume of 500 ul of buffer containing 50 mM Tris-HCl (pH 7.4 at room temperature), 0.1% bovine serum albumin, 2 mM mangenese chloride, 40 ug/ml bacitracin, 4 $\mu$g/ml leupeptin and chymostatin, 10 $\mu$M thiorphan and various doses of the putative tachykinin antagonists. Incubations are performed at room temperature for 90 min ($NK_1$ receptor assays) or 2 hr ($NK_2$ receptor assay)i; binding is terminated by addition of 50 mM Tris-HCl buffer (pH 7.4, 4° C.) and filtration under vacuum through GF/B filters presoaked with 0.1% polyethyleneimine ($NK_1$ receptor assays) or 0.5% bovine serum albumin ($NK_2$ receptor assay). Filter bound radioactivity is quantitated in a gamma counter. Nonspecific binding is defined as binding in the presence of 1 $\mu$M substance P or neurokinin A. Specific binding is calculated by subtracting nonspecific binding from total binding. Competition of iodinated SP or NKA binding by test compounds or standards is expressed as a percentage of this maximum binding. $IC_{50}$ values (concentration required to inhibit 50% of receptor binding) are generated for each of the test compounds by nonlinear regression using an iterative curve fitting program (GraphPAD Inplot, San Diego, Calif.).

EXAMPLE B

Antagonism of tachykinin-induced phosphatidylinositol (PI) turnover in vitro by putative antagonists One skilled in the art can also determine the potency of $NK_1$ receptor and $NK_2$ receptor antagonism in vitro as follows. Tachykinin-mediated phosphatidylinositol (PI, inositol phosphate) accumulation is measured in UCll or SKLKB82#3 cells in the presence and absence of $NK_1$ or $NK_2$ receptor antagonists, respectively. Tissues are incubated in Krebs-Henseleit buffer at 37° C. with 95% oxygen — 5% carbon dioxide gassing. Tissues are then incubated with fresh buffer containing 100 $\mu$Ci of myo-[2-$^3$H(N)] inositol at 37° C. for 60 min with gentle gassing. After washing twice in 5 ml room temperature buffer containing 10 mM lithium chloride, tissues are incubated for 30 min at room temperature with a buffer change at 15 min. Buffer is removed and Krebs-Henseleit buffer (containing 40 μg/ml bacitracin, 4 μg/ml each of leupeptin and chymostatin, 0.1% bovine serum albumin and 10 μM of thiorphan and 10 mM of lithium chloride) including the test compound is added. After 15 min, SP is added to UCII cells or NKA to SKLKB82#3 cells at various concentrations to start the reaction. After incubation for 60 min at room temperature the reaction is terminated by addition of 930 μl chloroform: methanol (1:2 by volume) to each tube, followed by 310 μl chloroform and 310 μl doubly distilled water. Samples are vortexed, centrifuged, and 0.9 ml of the aqueous (top) phase removed and added to 2 ml doubly distilled water. The mixture is vortexed and loaded onto a 50% Bio-Rad AG 1-X8 (formate form, 100–200 mesh) exchange column (Bio-Rad Laboratories, Hercules, Calif.). The columns are washed, in order, with: 1) 10 ml doubly distilled water, 2) 5 ml of 5 mM disodium tetraborate/60 mM sodium formate, and 3) 5 ml of 1M ammonium formate/0.1M formic acid. The third elution is collected and 1 ml counted in 7 ml scintillation fluid. A 50 μl aliquot of the organic (bottom) phase is removed, dried in a scintillation vial and counted in 7 ml scintillation fluid.

The ratio of DPM in the aqueous phase aliquot (total inositol phosphates) to the DPM in the 50 μl organic phase aliquot (total [$^3$H] inositol incorporated) is calculated for each sample. Data are expressed as a percent of agonist-induced accumulation of [$^3$H]-inositol phosphates over basal levels. The ratios in the presence of test compound and/or standards are compared to the ratios for control samples (i.e. no stimulating agonist).

Dose-response graphs are constructed and the ability of the test compounds to inhibit tachykinin-induced phosphatidyinositol turnover determined with the aid of a computer program. Data is expressed as percent stimulation of total inositol phosphate accumulation over basal levels and normalized to the maximum response produced by the tachykinin. Schild analysis is performed using dose response curves to obtain a value indicative of the strength of a competitive antagonist and is expressed as the $pA_2$, which is the negative logarithm of the molar concentration of antagonist which reduces the effect of a dose of agonist to one-half of that expected at the dose of agonist. When the slope of the lines obtained by a Schild analysis are not significantly different from one (1) the compound is acting as a competitive antagonist.

EXAMPLE C
Evaluation of $NK_1$ antagonism in vivo

One skilled in the art can also determine that the compounds of the present invention are $NK_1$ receptor antagonists in vivo by evaluating the compound's ability to inhibit substance P-induced plasma protein extravasation in guinea pig trachea. Substance P-induced protein leakage through postcapillary venules is assessed by measuring Evans Blue dye accumulation in guinea pig trachea. Animals are anesthetized with pentobarbital then injected with Evans Blue dye (20 mg/kg, i.v., prepared in 0.9% sodium chloride solution). One minute after dye administration, the antagonist is administered (i.v.) followed by substance P (1.0 nmole/kg, i.v.) and, after 5 min, excess dye removed from the circulation by transcardiac perfusion with 50 ml 0.9% sodium chloride solution. The trachea and primary bronchi are removed, blotted dry and weighed.

Dye quantitation is performed spectrophotometrically (620 nm) after extracting tissues in formamide for 24 hr at 50° C. Values are subtracted from background (dye only, no agonist). $ED_{50}$ (dose of compound which inhibits substance P-induced plasma protein extravasation by 50%) is calculated from linear regression analysis.

EXAMPLE D
Evaluation of $NK_2$ antagonism in vivo

One skilled in the art can determine that the compounds of the present invention are $NK_2$ receptor antagonists in vivo by evaluating the compound's ability to inhibit bronchoconstriction produced by a selective $NK_2$ receptor agonist, [β-Ala$^8$] NKA 4–10 in guinea pigs. Animals are anesthetized with urethane and then cannulated via the jugular vein, carotid artery, and trachea. The carotid cannula is connected to t Statham pressure transducer to measure blood pressure and the catheter placed into the jugular vein is used to administer the test compounds. The trachea cannula is inserted into a T-connector, one arm of the T-connector is connected to a respiratory pump while the other arm is connected to another pressure transducer. The respiratory pump is, adjusted to deliver 64 strokes per minute and the volume of air delivered is such that the insulation pressure is 10 cm of water. Animals are permitted to acclimate for about 15 minutes until stable breathing and blood pressure is obtained. Putative tachykinin antagonists or vehicle are administered i.v. and the line flushed with water. Dose response curves are then generated for the $NK_2$ receptor selective antagonist, [β-Ala$^8$] NKA 4–10, at doses ranging form 1–30 nmole/kg, i.v. Bronchoconstriction is inferred from the dose-dependent increase in pulmonary insulation pressure which occurs in response to the agonists. Antagonism of test compounds is inferred from a shift in the agonist dose-response curve to the right and suppression of the maximum insulation pressure produced in response to [βAla$^8$] NKA 4–10.

EXAMPLE E
Evaluation of $NK_1$ and $NK_2$ antagonism in vivo

One skilled in the art can determine that the compounds of the present invention are $NK_2$ receptor antagonists in vivo by evaluating the compounds ability to inhibit capsaicin-induced respiratory effects, which is known to release both SP and NKA from airway sensory nerves. Antagonism of capsaicin induced respiratory effects in conscious guinea pigs is carried out as follows. In vivo experiments are performed using male Dunkin Hartley guinea pigs (250–350g). Changes in conscious breathing patterns are monitored in four animals simultaneously using modified whole body plethysmography consisting of four small plexi-glass boxes each connected to a reference box via Validyne DP 45–16 differential pressure transducers. The 4 boxes are equipped with an air supply line (also used for aerosol delivery) and an exhaust air line. Supply and exhaust lines are of the same length and narrow bore and arise from a common supply chamber and are vented to a common exhaust chamber. This system is used to ensure that fluctuations in supply air and atmospheric pressure remain in phase and are eliminated from the net signal by the differential pressure transducers. The analog pressure signals are digitalized via a Data Translation DT2821 A to D board. Data are collected at a rate of 100 samples/second/animal. Each cycle of pressure change is analyzed using the following parameters: rising and falling slope determined between minimum and maximum pressures, the ratio of rising over falling slope, and the magnitude of the change between initial trough pressure and peak cycle pressure. Using these values (and observing the animals) the pressure cycles are characterized into normal breaths, forced exhalations (apparent by abdominal heaving), significant respiratory events (SREs; usually coughs, less often sneezes or gasps which are characterized by transient, extremely large pressure increases which are distinguishable from noise) and movement/noise with a PCAT 286 running a System V UNIX operating system. Dyspnea is defined as a significant, sustained increase in plethysmograph pressure which is associated with an observable shift to labored breathing in the animal.

During the course of a typical experiment in which airway responsiveness to various bronchoconstricting agents is examined, aerosols are delivered for 19 min (0.33 ml/min) using a DeVilbiss Ultraneb 99 ultrasonic nebulizer and animals monitored during this time. Prior to nebulization, 1 min of resting breathing is collected to establish a baseline pressure. In preliminary experiments, various concentrations of capsaicin were evaluated and the concentration of 0.001% chosen which maximized the number of animals exhibiting dyspnea but minimized the severity of the response. Putative tachykinin antagonists are administered (i.v.) 20 minutes prior to onset of aerosol exposure or orally 1 hour prior to onset of aerosol exposure.

Tachykinin receptor binding ($IC_{50}$ values) for representative compounds of the present invention are found in Table 1. Specifically, $NK_1$ and $NK_2$ receptor binding values were determined by the method of present Example A. These values represent the mean of several experiments. In Table 1, Compounds A and B are the compounds of present Examples 5.6 and 8.2, respectively, and Compound C, (+)-1-(2-(3-(3,4-dichloro-phenyl)-1-(3,4,5-trimethoxy-benzoyl)-pyrrolidin-3-yl)-ethyl)-4-phenyl-piperidine-4-carboxylic acid amide hydrochloride, the compound described in Example 20A.1 of PCT Publication No. WO 94/26735.

TABLE 1

| Compound | Tachykinin Receptor Binding | |
|---|---|---|
| | $NK_1$ $IC_{50}$ (nM) | $NK_2$ $IC_{50}$ (nM) |
| A | 2.79 | 16.3 |
| B | 3.15 | 232 |
| C | 3.04 | 8.17 |

EXAMPLE F

Evaluation of metabolism in human and guinea pig liver

One skilled in the art can determine the metabolic stability for the compounds of the present invention by determining the rate of disappearance of the test compound in vitro in liver extracts. Metabolic stability is inversely related to the rate of metabolism which can be evaluated by determining the rate of disappearance of the test compounds during the initial linear phase of this assay.

This method is carried out using either S9 or S10 liver supernatant obtained from either guinea pig or human liver. Guinea pig liver S9 can be purchased from Vitro Technologies, Baltimore, Md. and human liver S9 can be purchased from IIAM, Eaton Pa. Both guinea pig and human S10 supernatant can be prepared as follows: Combine weighed liver (fresh or stored at −80° C. until use) and 1.15% aqueous potassium chloride solution (10–15 mL) and homogenize using a PCU Poltron from Kinematics of Switzerland or equivalent. Combine the homogenate with 1.15% aqueous potassium chloride solution, sufficient so that 3 mL of solution (total) is used per mg of liver, and mix. Store the above homogenate on ice at all times prior to use and at −80° C. for long term storage.

Centrifuge a 20 mL volume of the homogenate at 12,500 rpm (10,000×gravity) at 3° C. After 20 minutes, remove the cover of white lipid protein, if present, and transfer the supernatant to a clean centrifuge tube. Centrifuge the supernatant at 12,500 (10,000×gravity) at 3° C. for 20 minutes before transfer to a clean storage vessel to give the S10 supernatant. Store the S10 supernatant on ice or at −80° C. for long term storage.

Prepare a stock solution of each test compound in methanol, such that 0.1 mL of the stock solution when spiked into 16 mL of incubation mixture yields an initial concentration of 10 μM of the test compound. Using this method the methanol content of the final incubation mixture will not exceed 1%.

Prepare the incubation mixture by combining in an incubation beaker S9 or S10 supernatant (4 mL); an aqueous solution containing 1.1 mM NADP, 6.4 nM glucose-6-phosphate, and 1.3 mM magnesium sulfate (4 mL); and an aqueous solution of glucose-6-phosphate (4 units/2 mL) (0.32 mL); and an aqueous 0.1M dipotassium monohydrogen phosphate solution (7.58 mL). Incubate the test compound by adding 0.1 mL of the stock solution of test compound to an incubation mixture, placed in a shaking water bath at 37° C.

To determine the rate of disappearance of test compounds in this assay, remove triplicate aliquots (0.5 mL) from the incubation beaker at 1, 3, 5, 10, 15, 30, and 60 minutes. Freeze all aliquots in a hexane/dry-ice slurry to instantly deactivate the enzymes. Store at −70° C. until assayed. The concentration of test compound in each aliquot is determined by HPLC after preparation and as compared to a standard concentration of test compound, such preparations and determinations are well known and appreciated in the art. The rate of disappearance can be determined from the slope of the initial linear phase of this assay by graphing the change in concentration of test compound vs. time.

The metabolic stability of Compounds A and B, the compounds of present Examples 5.6 and 8.2, respectively, and Compound C, (+)-1-(2-(3-(3,4-dichloro-phenyl)-1-(3,4,5-trimethoxy-benzoyl)-pyrrolidin-3-yl)-ethyl)-4-phenyl-piperidine-4-carboxylic acid amide hydrochloride, the compound described in Example 20A.1 of PCT Publication No. WO 94/26735 were determined by the method of Example F. These studies show that the present compounds are not substantially metabolized by liver oxidative enzymes.

Calibration standards for Compound A were prepared as follows: dissolve 10 mg of Compound A (free base) in methanol (10 mL) to give a 1 mg/mL stock solution. Use acetonitrile to dilute 1 mL of stock solution to 10 mL to give a 100 μg/mL spiking standard and serially dilute the 100 μg/mL solution with acetonitrile to give spiking standards having concentrations of 50, 25, 10, 5, 2.5, and 1.0 μg/mL. Calibration standards having concentrations of 10,000; 5,000; 2,500; 1,000; 500; 250; and 100 ng/mL are prepared in duplicated by adding 20 μL of each spiking standards to 0.2 mL of control S9 supernatant. Blanks and samples each receive 20μL of acetonitrile. Calibration standards and aliquots from that assay of compound A were prepared and evaluated as follows: charge a purple sulfonic acid solid phase extraction cartridge (Varian Inc., Harbor City, Calif.) with methanol (1 mL) and an aqueous 0.5% monochloroacetic acid solution (1 mL). Dilute the 0.2 mL of calibration standard or aliquot from the incubation with aqueous 5% acetonitrile (0.5 mL) and add to the charged cartridge. Pull the sample through the cartridge using vacuum, rinse with aqueous 0.5% monochloroacetic acid solution (1 ml,), aqueous 50% acetonitrile solution (50 mM potassium hydroxide) (1 mL). Elute into HPLC vial using 60% methanol, 38% water, 1% acetic acid, 1% triethylamine (0.4 mL). Analyze by HPLC using a TSK Super ODS column (2 micron, 5 cm×4.6 mm) (Tosohaas Inc. Montgomeryville, Pa.), column temperature 60° C., 0.15 mL injection, 210 nm detection, and eluting with 60% (10% acetonitrile, 90% water (25 mM potassium dihydrogen phosphate, pH 3)) and 40% (60% acetonitrile, 40% water (25 mM potassium dihydrogen phosphate, pH 3)) at 1.25 mL/minute.

Calibration standards for Compound B were prepared as follows: Combine 1.1 mg of Compound B and acetonitrile (9 mL) in a 10 mL volumetric flask. Sonicate for about 5 minutes to dissolve. Adjust the dilution to 10 mL and mix to give a 110 μg/mL spiking standards. Dilute 2 mL of stock solution with an equal volume of acetonitrile to give a μg/mL 55 spiking standard. Similar dilution gives 25, 12.5, 6.25, 3.125, 1.56, and 0.78 μg/mL spiking solutions. Calibration standards having concentrations of 10, 5, 2.5, 1.25, 0.625, 0.313, 0.156, 0.078 μg/mL are prepared by adding 50 μL of each spiking standards to 0.5 mL of control S9 supernatant. Calibration standards and aliquots from that assay of compound B were prepared and evaluated as follows: add a 20% trichloroacetic acid in acetonitrile solution (0.1 mL) to a 0.5 mL aliquot from the incubation (sample or control). Add 50 μL of each spiking standards or add acetonitrile (50 μL) to samples and blanks and vortex for 30 seconds before centrifuging at 12,000 rpm for 5 to 6 minutes. Transfer 300 μL of supernatant to HPLC vials and analyze by HPLC using a Rainin Microsorb column (3 micron, 100 mm×4.6 mm) (Rainin, Inc., Woborn, Mass.), at a column temperature of 60° C., 0.15 mL injection, 216 nm detection, and elute with 88% (20% acetonitrile, 79.15% water, 0.6% acetic acid, 0.25 triethylamine) and 12% (80% acetonitrile, 19.5% water, 0.6% acetic acid, 0.25 triethylamine) at 1.0 mL/minute.

Calibration standards for Compound C were prepared as follows: dissolve 1.0 mg of Compound C (free base) in acetonitrile (10 mL) to give a 100 μg/mL stock solution. Serially dilute the 100 μg/mL solution with acetonitrile to give spiking standards 50, 25, 10, 5, 2.5, and 1.0 μg/mL. Calibration standards having concentrations of 10,000; 5,000; 2,500; 1,000; 500; 250; and 100 ng/mL are prepared in duplicated by adding 20 μL of each spiking standards to 0.2 mL of control S9 supernatant. Blanks and samples receiving 20 μL of acetonitrile. Calibration standards and aliquots from that assay of Compound C were prepared and evaluated as follows: charge a purple sulfonic acid solid phase extraction cartridge (Varian Inc., Harbor City, Calif.) with methanol (1 mL) and an aqueous 0.5% monochloroacetic acid solution (1 mL). Dilute the 0.5 mL of calibration standard or aliquot from the incubation with aqueous 5% acetonitrile (0.5 mL) and add to the charged cartridge. Pull the sample through the cartridge using vacuum, rinse with aqueous 0.5% monochloroacetic acid solution (1 mL), aqueous 50% acetonitrile solution (1 mL). Elute into HPLC vial using 60% methanol, 38% water, 1% acetic acid, 1% triethylamine (0.4 mL). Analyze by HPLC using a TSK Super ODS column (2 micron, 5 cm×4.6 mm) (Tosohaas Inc. Montgomeryville, Pa.), column temperature 60° C., 0.2 mL injection, 210 nm detection, and elute with 60% (10% acetonitrile, 90% water (25 mM potassium dihydrogen phosphate, pH 3)) and 40% (60% acetonitrile, 40% water (25 mM potassium dihydrogen phosphate, pH 3)) at 1.25 mL/minute.

The metabolic stability for the compounds of the present invention is shown by data from metabolism rate studies in guinea pig S9 liver supernatant and human S9 liver supernatant for representative compounds of the present invention. The results are found in Tables 2 and 3, respectively. In Table 2, Compounds A and B are the compounds of present Examples 5.6 and 8.2, respectively, and Compound C, (+)-1-(2-(3-(3,4-dichloro-phenyl)-1-(3,4,5-trimethoxy-benzoyl)-pyrrolidin-3-yl)-ethyl)-4-phenyl-piperidine-4-carboxylic acid amide hydrochloride, the compound described in Example 20A.1 of PCT Publication No. WO 94/26735. The compounds of the present invention are distinguished by a substantial lack of metabolism as shown by their nearly constant concentration during the initial phase linear phase, in particular, in comparison to the compounds of PCT Publication No. WO 94/26735, as can be seen from Table 2, below.

TABLE 2

| Time | Metabolic Stability in Guinea Pig Liver S9, concentration (μg/mL) | | |
|---|---|---|---|
| (min.) | Compound A | Compound B | Compound C |
| blank | | | |
| 1 | 6.1 | 6.2 | 6.3 |
| 3 | 6.6 | 6.4 | 6.0 |
| 5 | 6.3 | 6.4 | 5.3 |
| 10 | 6.1 | 6.3 | 4.8 |
| 15 | 6.1 | 6.3 | 4.0 |
| 30 | 6.3 | 6.3 | 3.8 |
| 60 | 6.9 | 6.2 | 3.5 |

TABLE 3

| Time | Metabolic Stability in Human Liver S9, concentration (μg/mL) | | |
|---|---|---|---|
| (min.) | Compound A | Compound B | Compound C |
| blank | | | |
| 1 | 6.6 | 6.4 | 6.2 |
| 3 | 6.5 | 6.6 | 5.6 |
| 5 | 6.6 | 6.1 | 5.9 |
| 10 | 6.7 | 6.1 | 5.2 |
| 15 | 6.6 | 5.7 | 4.5 |
| 30 | 6.8 | 5.3 | 3.2 |
| 60 | 6.9 | 4.4 | 2.5 |

What is claimed is:

1. A compound of the formula

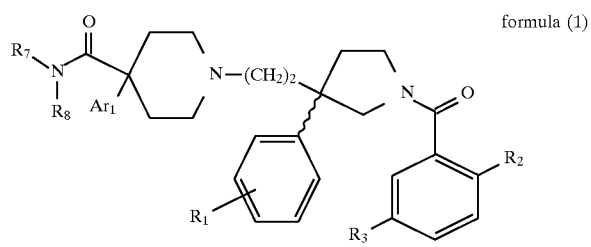

formula (1)

wherein $R_1$ is from 1 to 3 substituents each independently chosen from the group consisting of hydrogen, halogen, —$CF_3$, $C_1$–$C_6$ alkyl, and $C_1$–$C_6$ alkoxy;

$R_2$ is from chosen from the group consisting of hydrogen, $C_1$–$C_4$ alkyl, and $C_1$–$C_4$ alkoxy;

R₃ is a radical

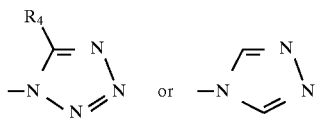 or wherein

R₄ is selected from the group consisting of hydrogen, C₁–C₄ alkyl, and —CF₃;

Ar₁ is a radical selected from the group consisting of

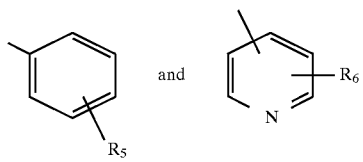

wherein

R₅ is from 1 to 3 substituents each independently chosen from the group consisting of hydrogen, halogen, —CF₃, C₁–C₆ alkyl, and C₁–C₆ alkoxy;

R₆ is from 1 to 2 substituents each independently chosen from the group consisting of hydrogen, halogen, C₁–C₆ alkyl, and C₁–C₆ alkoxy;

R₇ and R₈ are hydrogen or together with the nitrogen to which they are attached form a piperidine, morpholine, piperazine, 4-methylpiperazine, or pyrrolidine ring;

and stereoisomers, and pharmaceutically acceptable salts thereof.

2. A compound of claim 1 wherein R₃ is a radical selected from the group consisting of

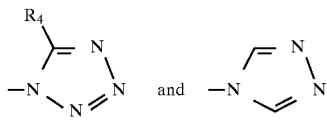

wherein R₄ is as defined in claim 1.

3. A compound of claim 2 wherein R₃ is the radical

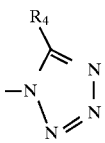

wherein R₄ is as defined in claim 1.

4. A compound of claim 3 wherein R₄ is hydrogen.

5. A compound of claim 4 wherein R₂ is methoxy.

6. A compound of claim 5 wherein R₁ is 3,4-dichloro.

7. A compound of claim 6 wherein R₇ and R₈ are hydrogen.

8. A compound of claim 1 wherein the compound is (R)- or (S)-1-(2-methoxy-5-(1H-tetrazol-1-yl)benzoyl)-3-(2-(4-phenyl-4-carboxamidopiperidin-1-yl)ethyl)-3-(3,4-dichlorophenyl)pyrrolidine or a mixture thereof.

9. A compound of claim 8 wherein the compound is (R)-1-(2-methoxy-5-(1H-tetrazol-1-yl)benzoyl)-3-(2-(4-phenyl-4-carboxamidopiperidin-1-yl)ethyl)-3-(3,4-dichlorophenyl)pyrrolidine.

10. A compound of claim 1 wherein the compound is (R)- or (S)-1-(2-methoxy-5-(1H-tetrazol-1-yl)benzoyl)-3-(2-(4-(pyrid-3-yl)-4-carboxamidopiperidin-1-yl)ethyl)-3-(3,4-dichlorophenyl)pyrrolidine or a mixture thereof.

11. A compound of claim 10 wherein the compound is (R)-1-(2-methoxy-5-(1H-tetrazol-1-yl)benzoyl)-3-(2-(4-(pyrid-3-yl)-4-carboxamidopiperidin-1-yl)ethyl)-3-(3,4-dichlorophenyl)pyrrolidine.

12. A pharmaceutical composition comprising a compound of claim 1 and a pharmaceutically acceptable carrier.

13. A method for treating asthma in a patient in need thereof comprising administering to said patient a therapeutically effective amount of a compound of claim 1.

14. A method for treating cough in a patient in need thereof comprising administering to said patient a therapeutically effective amount of a compound of claim 1.

15. A method for treating bronchitis in a patient in need thereof comprising administering to said patient a therapeutically effective amount of a compound of claim 1.

16. A method for treating pain in a patient in need thereof comprising administering to said patient a therapeutically effective amount of a compound of claim 1.

* * * * *